(12) United States Patent
Ikuyama

(10) Patent No.: US 10,591,402 B2
(45) Date of Patent: Mar. 17, 2020

(54) IMAGE PROCESSING APPARATUS, IMAGE PROCESSING METHOD, AND IMAGE PROCESSING PROGRAM

(71) Applicant: KONICA MINOLTA, INC., Chiyoda-ku, Tokyo (JP)

(72) Inventor: Jun Ikuyama, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 141 days.

(21) Appl. No.: 15/573,194

(22) PCT Filed: May 13, 2016

(86) PCT No.: PCT/JP2016/064252
§ 371 (c)(1),
(2) Date: Nov. 10, 2017

(87) PCT Pub. No.: WO2016/190129
PCT Pub. Date: Dec. 1, 2016

(65) Prior Publication Data
US 2018/0128734 A1    May 10, 2018

(30) Foreign Application Priority Data

May 22, 2015 (JP) .................. 2015-104085

(51) Int. Cl.
*G01N 15/14* (2006.01)
*C12M 1/34* (2006.01)
(Continued)

(52) U.S. Cl.
CPC ........... *G01N 15/1463* (2013.01); *C12M 1/34* (2013.01); *C12Q 1/02* (2013.01); *G01N 21/17* (2013.01);
(Continued)

(58) Field of Classification Search
CPC ......... G06T 7/0012; G06T 7/11; G06T 11/60; G06T 11/80; G06T 2207/10056;
(Continued)

(56) References Cited

U.S. PATENT DOCUMENTS

2005/0058330 A1* 3/2005 Mitsuhashi ............ G06Q 50/22
382/128
2006/0285743 A1* 12/2006 Oh ........................ G06K 9/0014
382/170
(Continued)

FOREIGN PATENT DOCUMENTS

JP       3314759 B2    8/2002
JP       4500138 B2    7/2010
(Continued)

OTHER PUBLICATIONS

International Search Report for corresponding Application No. PCT/JP2016/064252; dated Aug. 2, 2016.
(Continued)

*Primary Examiner* — Katrina R Fujita
(74) *Attorney, Agent, or Firm* — Cantor Colburn LLP

(57) ABSTRACT

An object of the present invention is to provide a technology for more easily and accurately extracting overall cell regions from a cell morphological image. To achieve the object, first, an acquiring unit acquires a region-identifiable image for identifying a first cell region occupied by a specific portion of a cell in the cell morphological image capturing a shape of the cell using a first display element. Then, an adding unit adds, to the region-identifiable image, a second display element that identifies at least an outline portion of a second cell region occupied by a specific portion different from the first cell region in the cell morphological image depending on a predetermined signal set in advance and input in response to a user's operation. In addition, a correcting unit corrects the region-identifiable image such that the display
(Continued)

element that identifies the first cell region is displayed on the display unit for at least a part of the overlapping area where the first and second cell regions overlap each other.

19 Claims, 14 Drawing Sheets

(51) Int. Cl.
| | |
|---|---|
| *C12Q 1/02* | (2006.01) |
| *G01N 21/17* | (2006.01) |
| *G06T 11/80* | (2006.01) |
| *G01N 33/48* | (2006.01) |
| *G06T 7/00* | (2017.01) |
| *G06T 7/11* | (2017.01) |
| *G06F 3/14* | (2006.01) |
| *G06T 11/60* | (2006.01) |
| *G01N 15/10* | (2006.01) |

(52) U.S. Cl.
CPC ............... *G01N 33/48* (2013.01); *G06F 3/14* (2013.01); *G06T 7/0012* (2013.01); *G06T 7/11* (2017.01); *G06T 11/60* (2013.01); *G06T 11/80* (2013.01); *G01N 2015/1006* (2013.01); *G01N 2015/1497* (2013.01); *G06T 2207/10056* (2013.01); *G06T 2207/20096* (2013.01); *G06T 2207/30024* (2013.01)

(58) Field of Classification Search
CPC ........... G06T 2207/20096; G06T 2207/30024; C12M 1/34; C12Q 1/02; G01N 15/1463; G01N 21/17; G01N 33/48; G01N 2015/1006; G01N 2015/1497; G06F 3/14
See application file for complete search history.

(56) References Cited

U.S. PATENT DOCUMENTS

| | | | | |
|---|---|---|---|---|
| 2010/0150443 | A1* | 6/2010 | Zahniser | G06K 9/342 |
| | | | | 382/173 |
| 2011/0212486 | A1* | 9/2011 | Yamada | G02B 21/365 |
| | | | | 435/40.5 |
| 2012/0122143 | A1* | 5/2012 | Mimura | C12M 41/14 |
| | | | | 435/29 |
| 2012/0134571 | A1* | 5/2012 | Ito | G06T 1/00 |
| | | | | 382/133 |
| 2014/0307930 | A1 | 10/2014 | Lee | |
| 2017/0370901 | A1* | 12/2017 | Ichitani | G01N 33/48 |
| 2018/0038796 | A1* | 2/2018 | Ichitani | G01N 33/48 |

FOREIGN PATENT DOCUMENTS

| | | |
|---|---|---|
| JP | 2011179924 A | 9/2011 |
| JP | 4801025 B2 | 10/2011 |
| JP | 4825222 B2 | 11/2011 |

OTHER PUBLICATIONS

Written Opinion of the International Searching Authority for corresponding Application No. PCT/JP2016/064252; dated of Aug. 2, 2016.

Daniela Furrer et al., "Validation of a new classifier for the automated analysis of the human epidermal growth factor receptor 2(HER2) gene amplification in breast cancer specimens," Diagnostic Pathology, pp. 1-10, 2013.

Extended European Search Report corresponding to Application No. 16799837.6-1210/3299811 PCT/JP2016064252; dated Apr. 24, 2018.

JPO Notice of Reasons for Refusal corresponding to Application No. 2017-520626; dated Jun. 11, 2019.

* cited by examiner

IMAGE PROCESSING APPARATUS, IMAGE PROCESSING METHOD, AND IMAGE PROCESSING PROGRAM

CROSS REFERENCE TO RELATED APPLICATIONS

This is the U.S. national stage of application No. PCT/JP2016/064252, filed on May 13, 2016. Priority under 35 U.S.C. § 119(a) and 35 U.S.C. § 365(b) is claimed from Japanese Applications No. 2015-104085, filed May 22, 2015, the disclosure of which is incorporated herein by reference.

TECHNICAL FIELD

The present invention relates to an image processing apparatus, an image processing method, and an image processing program, and more particularly, to a an image processing technology used for a cell morphological image capturing a cell shape.

BACKGROUND ART

A so-called pathological diagnosis is widely conducted, in which a tissue slice taken from a living body such as a human being or an animal is observed with a microscope to diagnose presence or absence of a lesion, a type of the lesion, and the like. In this pathological diagnosis, the tissue slice to be diagnosed is generally presented to microscope observation after being subjected to fixation, embedding, slicing, and staining sequentially in this order.

In recent years, a microscope observation technology has been provided, in which an image (also referred to as a "cell morphological image") capturing a shape of a biological tissue containing a plurality of cells is acquired, and the shape of the cell is automatically extracted from the cell morphological image through image processing (for example, see Patent Literatures 1 to 4).

For example, in Patent Literature 1, a pixel group serving as a candidate for a cell center is extracted from the cell morphological image, and only pixels suitable for the cell center in the pixel group are selected on the basis of a predetermined criterion. In addition, pixels that form an outline of the cell are selected based on position information of the selected cell center pixels and a concentration gradient direction of its neighboring pixels.

In Patent Literature 2, at least one of a point having a minimum or a maximum luminance, a point having a color different from those of the surrounding points, and a point having a maximum luminance gradient is extracted as an extraction point from the cell morphological image, and clustering for the extraction point is performed to determine the center and boundary of the cell.

In Patent Literature 3, pixels sorted on the basis of an attribute value range are added to a label image one by one from an end point of the attribute value range. In addition, when the feature calculated for each arranged object meets a predetermined allowable criterion, the object is output as an output image. In this case, each object in the image is identified by repeating addition of the pixels to the label image, evaluation of the feature of the created object, and output of the object until the stop point.

In Patent Literature 4, a group of cells having the feature similar to that of a specific cell of interest specified by a user are automatically extracted from a plurality of cells of the cell morphological image subjected to a predetermined processing.

CITATION LIST

Patent Literature

Patent Literature 1: JP 3314759 B2
Patent Literature 2: JP 4500138 B2
Patent Literature 3: JP 4825222 B2
Patent Literature 4: JP 4801025 B2

SUMMARY OF INVENTION

Technical Problem

However, in the technique of Patent Literature 1, for example, the tissue slice presented for the pathological diagnosis is darkly dyed in some cases. In this case, it is difficult to select the pixels that form the cell outline using the concentration gradient.

In the technique of Patent Literature 2, for example, when the tissue slice is collected through needle biopsy, a plurality of cells are compressed, and the cells are liable to overlap with each other. In a case where a plurality of cells overlap each other vertically and horizontally, even when a center point of a plurality of grouped extraction points is set as the cell center as a representative point, the number of extraction points set as the cell center hardly match the actual number of cells.

In the technique of Patent Literature 3, for example, in a case where a so-called center blurring state exists, in which the outline of the cell nucleus is clearly recognized, but the inside of the cell nucleus is not clearly recognized, information on the inside of the cell nucleus becomes the same as information on portions other than the cell nucleus, so that the cell nucleus is erroneously detected.

In the technique of Patent Literature 4, since a plurality of cells in the cell morphological image are narrowed down to some cell groups, the number of cells extracted from the cell morphological image decreases.

As described above, in the techniques of Patent Literatures 1 to 3, a region relating to a cell (also referred to as a "cell region") is not accurately and completely extracted from the cell morphological image in some cases depending on a situation of the cell morphological image. In addition, the technique of Patent Literature 4 is originally a technique of narrowing down cells extracted from the cell morphological image, and the cell region is not extracted accurately and completely from the cell morphological image in many cases.

In view of the aforementioned problems, an object of the present invention is to provide a technology capable of more easily and accurately extracting overall cell regions from a cell morphological image.

Solution to Problem

In order to address the aforementioned problems, according to an aspect of the invention, there is provided an image processing apparatus including: a display control unit, an acquiring unit, an input unit, an adding unit, and a correcting unit. Here, the display control unit displays a cell morphological image capturing a cell shape. The acquiring unit acquires a region-identifiable image that identifies a first cell region occupied by a specific portion of the cell in the cell morphological image using a first display element. The input unit receives a signal responding to a user's operation. The adding unit adds, to the region-identifiable image, a second display element that specifies at least an outline portion of the second cell region occupied by the specific portion different from the first cell region in the cell morphological image depending on a predetermined signal set in advance and input to the input unit. The correcting unit corrects the region-identifiable image such that the display element that specifies the first cell region is displayed by the display control unit on the display unit for at least a part of the overlapping area where the first and second cell regions overlap each other.

According to another aspect of the invention, there is provided an image processing method including steps (a) to (c). Here, in step (a), an acquiring unit acquires a region-identifiable image for identifying a first cell region occupied by a specific portion of a cell in a cell morphological image capturing a shape of the cell using a first display element. In step (b), an adding unit adds, to the region-identifiable image, a second display element that identifies at least an outline portion of the second cell region occupied by the specific portion other than the first cell region in the cell morphological image depending on a predetermined signal set in advance and input in response to a user's operation. In step (c), correcting unit corrects the region-identifiable image such that the display element that identifies the first cell region is displayed on the display unit for at least a part of the overlapping area where the first and second cell regions overlap each other.

According to still another aspect of the invention, there is provided an image processing program executed by a control unit included in an information processing apparatus to cause the information processing apparatus to work as the image processing apparatus according to the aforementioned aspect.

Advantageous Effects of Invention

According to the invention, a user can easily add a display element that identifies a cell region by a user to the region-identifiable image that identifies cell regions occupied by a specific portion of the cell in the cell morphological image using display elements. Therefore, it is possible to more easily and accurately extract overall cell regions from the cell morphological image.

DESCRIPTION OF EMBODIMENTS

An embodiment of the invention and various modifications will now be described with reference to the accompa-

(1) First Embodiment

(1-1) Overview of Pathological Diagnosis Support System

Figure 1:
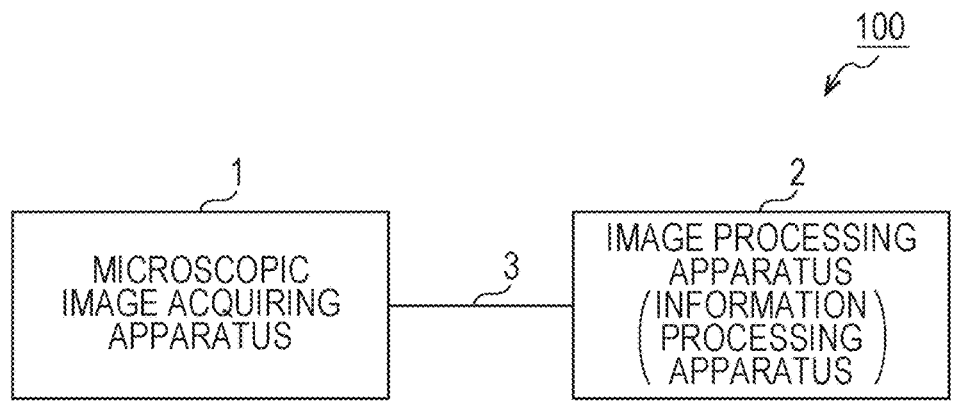
FIG. 1 is a diagram illustrating an exemplary schematic configuration of a pathological diagnosis support system.

FIG. 1 is a diagram illustrating a schematic configuration example of a pathological diagnosis support system 100 according to an embodiment. The pathological diagnosis support system 100 acquires a microscopic image by capturing a tissue slice of a living body stained with a predetermined staining reagent, performs image processing for this microscopic image, and then performs an analysis process for calculating a feature amount quantitatively representing expression of a specific biological substance in the tissue slice.

Here, the microscopic image includes, for example, an image capturing a cell shape in a tissue slice of a living body (also referred to as a "cell morphological image") and an image capturing a distribution of a specific biological substance existing in the cell slice of the living body (also referred to as a "substance distribution image"). The living body includes, for example, a human body, a non-human animal, and the like. The living body may also include animals in a broad meaning encompassing a human body and a non-human animal. The image processing includes, for example, a process performed on the microscopic image such that a feature amount quantitatively representing expression of a specific biological substance in the analysis process is obtained from the microscopic image with high accuracy.

According to this embodiment, since the image processing is performed such that overall cell regions capturing cells are more accurately extracted from the cell morphological image, it is possible to obtain, for example, the feature amount that quantitatively represents expression of a specific biological substance in a tissue slice in an analysis process with high accuracy.

As illustrated in FIG. 1, the pathological diagnosis support system 100 includes a microscopic image acquiring apparatus 1, an image processing apparatus 2, and a communication line 3 that data-communicably connects the microscopic image acquiring apparatus 1 and the image processing apparatus 2. The communication line 3 may be of a wire-based mode such as a cable or a wireless mode. Specifically, the communication line 3 may include, for example, a local area network (LAN) in which at least one of a wire-based mode and a wireless mode is employed. In addition, data communication between the microscopic image acquiring apparatus 1 and the image processing apparatus 2 may be implemented using various media such as a storage medium.

The microscopic image acquiring apparatus 1 is, for example, a camera-embedded optical microscope well known in the art. In the microscopic image acquiring apparatus 1, data on an image (also referred to as "microscopic image data") relating to an enlarged image of the tissue slice (also referred to as a "microscopic image") is obtained by photographing an optical image of a tissue slice on a slide glass placed on a stage, and the microscopic image data is transmitted to the image processing apparatus 2. Note that, in the following description, the microscopic image data and the microscopic image are collectively referred to as a "microscopic image."

Specifically, the microscopic image acquiring apparatus 1 includes, for example, an irradiating unit, an image forming unit, a photographing unit, a communication I/F, and the like. The irradiating unit has, for example, a light source, a filter, and the like to irradiate light onto the tissue slice on the slide glass placed on the stage. The image forming unit has, for example, an eyepiece lens, an object lens, and the like to form an image from transmission light, reflection light, or fluorescent light emitted from the tissue slice depending on irradiation of light onto the tissue slice of the slide. The photographing unit is, for example, a camera equipped with a charge coupled device (CCD) and obtains a microscopic image by photographing an optical image of the tissue slice formed on an image plane using the image forming unit. The communication I/F transmits the microscopic image to the image processing apparatus 2.

The microscopic image acquiring apparatus 1 includes a bright field unit in which an irradiating unit and an image forming unit suitable for bright field observation are combined, and a fluorescence unit in which an irradiating unit and an image forming unit suitable for fluorescent observation are combined. In addition, by switching the unit between the bright field unit and the fluorescence unit, the observation mode is switched between a bright field observation mode and a fluorescent observation mode. As a result, the microscopic image obtained by the microscopic image acquiring apparatus 1 contains, for example, a bright field image obtained through photographing in the bright field observation and a fluorescence image obtained through photographing in the fluorescent observation.

The "bright field image" is a microscopic image obtained by magnifying, image-forming, and photographing the tissue slice stained with a predetermined staining reagent in the bright field of the microscopic image acquiring apparatus 1. Here, the predetermined staining reagent may include, for example, a hematoxylin staining reagent (H staining reagent) and a hematoxylin-eosin staining reagent (HE staining reagent). The hematoxylin (H) is a blue-purple pigment and stains cell nucleuses, bone tissues, a part of cartilage tissues, and serous components (such as basophilic tissues), and the like. Eosin (E) is a red-pink pigment that stains cytoplasm, connective tissues of soft tissue, erythrocytes, fibrins, and endocrine granules (such as eosinophilic tissues), and the like. That is, according to this embodiment, the bright field image is a cell morphological image showing the cell shape in the tissue slice.

The "fluorescence image" is a microscopic image obtained by irradiating excitation light having a predetermined wavelength onto the tissue slice stained with a predetermined fluorescent staining reagent in the microscopic image acquiring apparatus 1 to generate fluorescent emission, and magnifying, image-forming, and photographing this fluorescent light. Here, the fluorescent staining reagent includes, for example, a staining reagent having fluorescent substance-containing nanoparticles to which a biological substance recognition portion that specifically binds and/or reacts with a specific biological substance is bound. The fluorescent substance-containing nanoparticles are nanoparticles containing a fluorescent substance (also referred to as "fluorescent particles"). Fluorescence appears in the fluorescence image as the fluorescent substance-containing nanoparticles (fluorescent substance) of the fluorescent staining reagent are excited to emit light to visualize expression of a specific biological substance corresponding to the biological substance recognition portion in the tissue slice. That is, according to this embodiment, the fluorescence image is a substance distribution image showing a distribution of a specific biological substance existing in cells of a living body.

The image processing apparatus 2 receives the microscope image transmitted from the microscopic image acquiring apparatus 1 and applies an image processing to this microscope image. The image processing apparatus 2 is implemented by executing a predetermined program in the information processing apparatus. In addition, the image processing apparatus 2 performs, for example, an analysis process for calculating a feature amount quantitatively representing expression of a specific biological substance in a tissue slice on the microscopic image subjected to the image processing.

(1-2) Functional Configuration of Information Processing Apparatus

Figure 2:
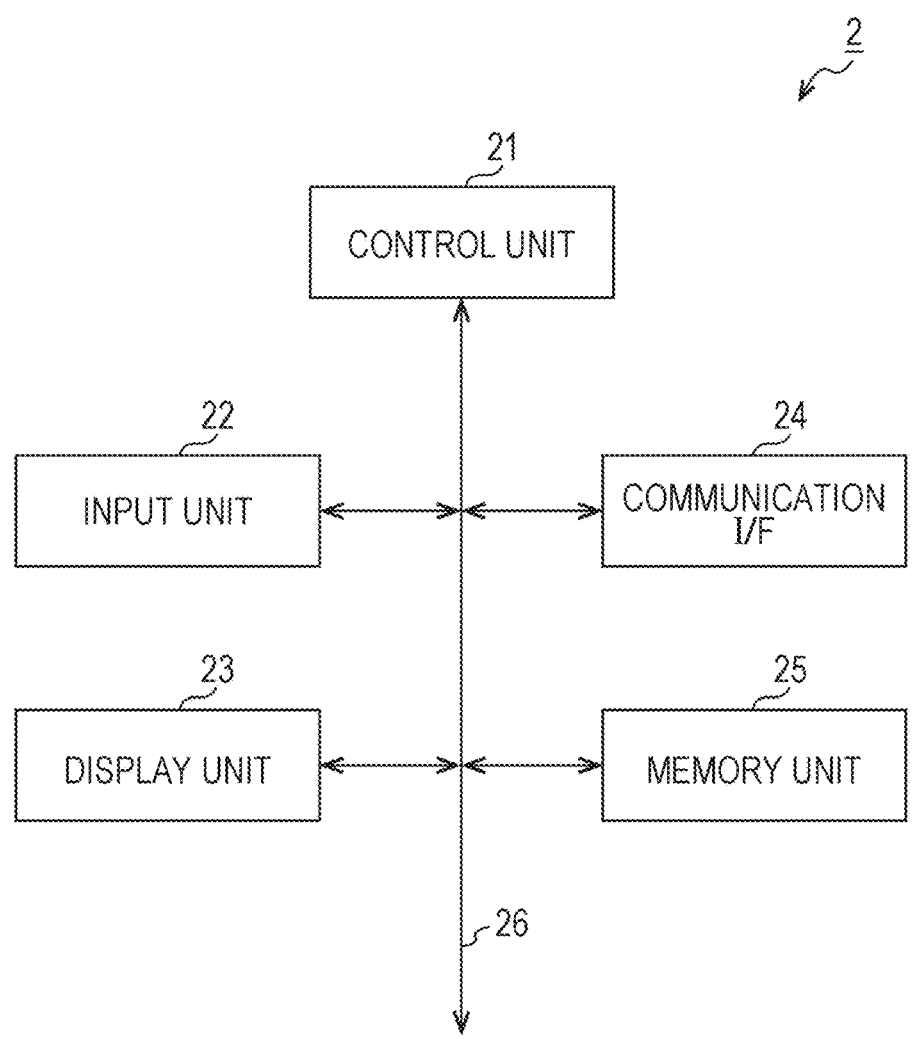
FIG. 2 is a block diagram schematically illustrating a functional configuration of an information processing apparatus.

FIG. 2 is a block diagram schematically illustrating a functional configuration of the information processing apparatus that implements functions of the image processing apparatus 2. As illustrated in FIG. 2, the information processing apparatus includes, for example, a control unit 21, an input unit 22, a display unit 23, a communication I/F 24, a memory unit 25, and the like. In addition, each unit 21 to 25 is connected to each other data-communicably via a bus 26.

The control unit 21 is an electric circuit provided with a processor, a memory, and the like. Here, the processor may include, for example, a central processing unit (CPU) or the like, and the memory may include a random access memory (RAM) as a volatile memory, or the like. The control unit 21 executes various processing in cooperation with various programs stored in the memory unit 25 and comprehensively controls operations of the information processing apparatus as the image processing apparatus 2. In addition, the control unit 21 causes the information processing apparatus to work as the image processing apparatus 2 by executing an image processing program P1 (FIG. 3) stored in the memory unit 25.

The input unit 22 receives a signal in response to the operation of the operator as a user for the image processing apparatus 2. Here, the input unit 22 may be a manipulation unit that receives a signal in response to a user's manipulation (also referred to as a "manipulation signal") or may be a voice input unit that receives a signal in response to a user's voice (also referred to as an "audio signal"). The manipulation unit may include a keyboard provided with character input keys, numeric input keys, various function keys, and the like, and a pointing device such as a mouse or a touch pen. Using the manipulation unit, for example, a manipulation signal responding to depression of the key on the keyboard and a manipulation signal responding to a manipulation of the pointing device may be input to the control unit 21.

The display unit 23 displays various images depending on the signal input from the control unit 21. The display unit 23 includes a display device such as a cathode ray tube (CRT) and a liquid crystal display (LCD).

The communication I/F 24 is an interface for communicating data with external devices placed outside the image processing apparatus 2. The external device includes, for example, the microscopic image acquiring apparatus 1. For this reason, the communication I/F 24 serves as a receiver for receiving the microscopic images from the microscopic image acquiring apparatus 1, for example. Note that, for example, the image processing apparatus 2 may be provided with a LAN adapter, a router, or the like to communicate with external devices via a communication network such as the LAN.

The memory unit 25 stores various programs, various data, and the like. The memory unit 25 may include, for example, a hard disk drive (HDD), a nonvolatile semiconductor memory, or the like.

(1-3) Functional Configuration of Image Processing Apparatus

Figure 3:
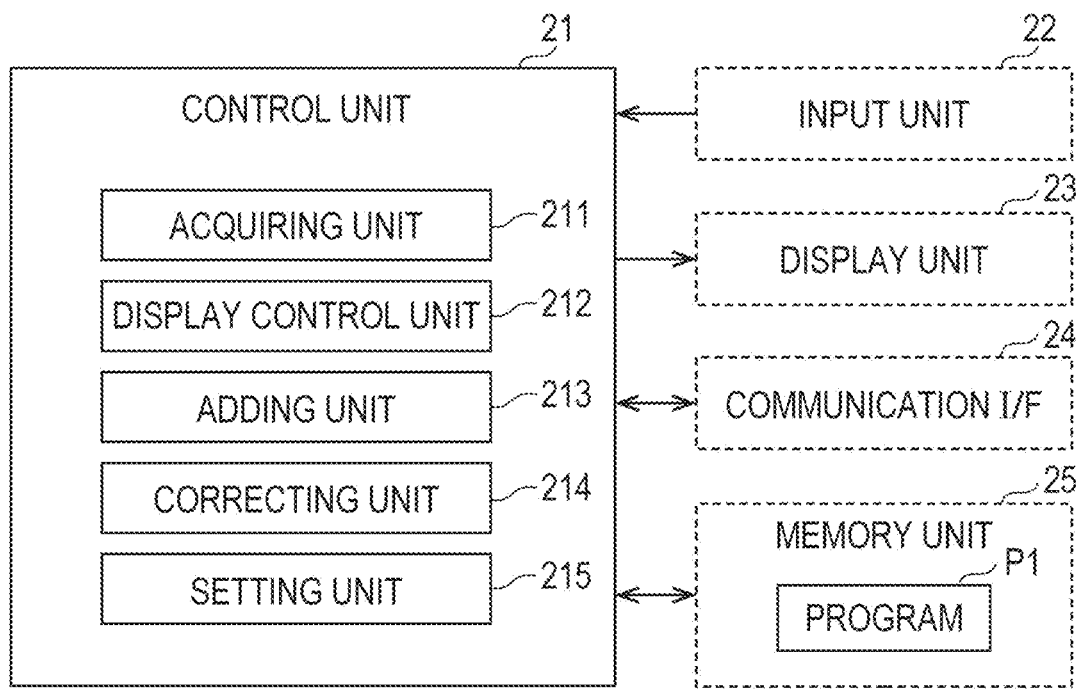
FIG. 3 is a block diagram exemplifying a functional configuration implemented by a control unit.

FIG. 3 is a block diagram illustrating a functional configuration implemented by the control unit 21 of the image processing apparatus 2. In the control unit 21 included in the information processing apparatus, the information processing apparatus serves as the image processing apparatus 2 as the image processing program P1 stored in the memory unit 25 is executed. In this case, as illustrated in FIG. 3, the image processing apparatus 2 has an acquiring unit 211, a display control unit 212, an adding unit 213, a correcting unit 214, and a setting unit 215 as a functional configuration implemented by the control unit 21.

Figure 4:
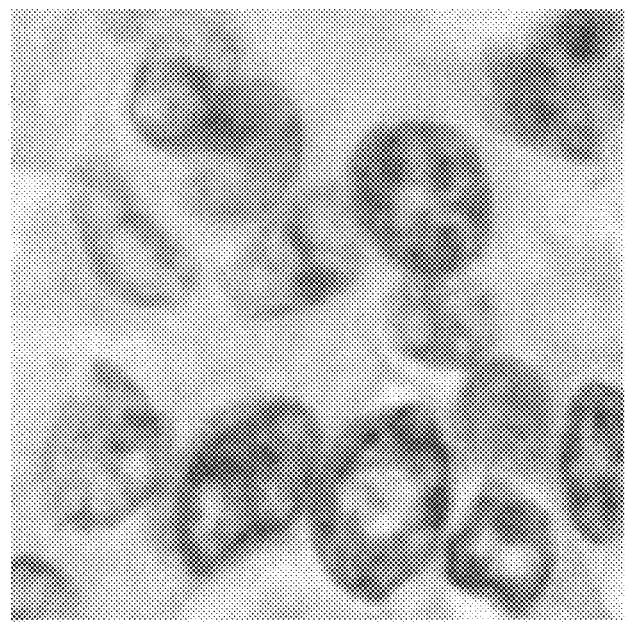
FIG. 4 is a diagram illustrating an exemplary cell morphological image.

The acquiring unit 211 acquires an image (also referred to as a "region-identifiable image") in which a region occupied by a specific portion of cells in the cell morphological image (also referred to as a "first cell region") is identified by a predetermined display element (also referred to as a "first display element"). According to this embodiment, a case where the specific portion is a cell nucleus will be described by way of example. FIG. 4 is a diagram illustrating an exemplary cell morphological image.

The acquiring unit 211 acquires the region-identifiable image, for example, through a predetermined image processing for the cell morphological image input from the communication I/F 24. Here, as the predetermined image processing, for example, a process of detecting a region occupied by a specific portion in the cell morphological image using at least one of binarization such as a discriminant analysis method and a P-tile method and clustering such as a k-averaging method and an EM algorithm may be employed. For example, a process of detecting a region occupied by a specific portion in the cell morphological image on the basis of learning contents obtained through machine learning using feature amounts of many types of images may be employed. Furthermore, the acquiring unit 211 may acquire, as the first cell region, a region satisfying other criteria such as circularity, size, and color in the cell morphological image among regions once detected from the cell morphological image on the basis of binarization, clustering, machine learning, and the like.

Figure 5:
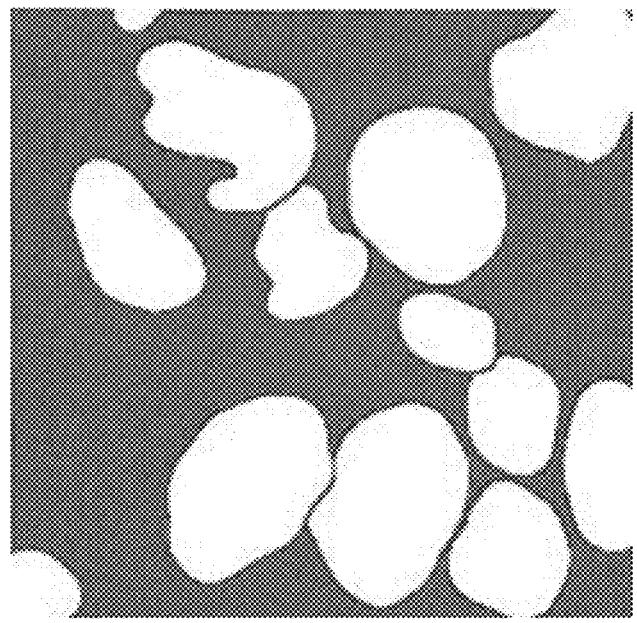
FIG. 5 is a diagram illustrating an exemplary region-identifiable image.

Here, as the region-identifiable image, for example, an image in which a region occupied by a specific portion and a region other than that region distinguishably appear with respect to the cell morphological image may be employed. Specifically, for example, the region occupied by a specific portion is indicated by a first display element appearing with a predetermined color (also referred to as a "first color") or hatching, and the region occupied by parts other than the specific portion appear with a color (also referred to as a "second color") or hatching different from that of the first display element. Here, for example, blue, gray, or the like may be employed as the first color, and white, black, or the like may be employed as the second color. FIG. 5 is a diagram illustrating an exemplary region-identifiable image acquired through binarization for the cell morphological image of FIG. 4.

The display control unit 212 displays various images on the display unit 23. Various images include, for example, a cell morphological image, a region-identifiable image, and the like. Here, various images may be displayed on the display unit 23, for example, as data of various images are output from the display control unit 212 to the display unit 23. For example, the cell morphological image of FIG. 4 and the region-identifiable image of FIG. 5 are displayed on the display unit 23.

Figure 6:
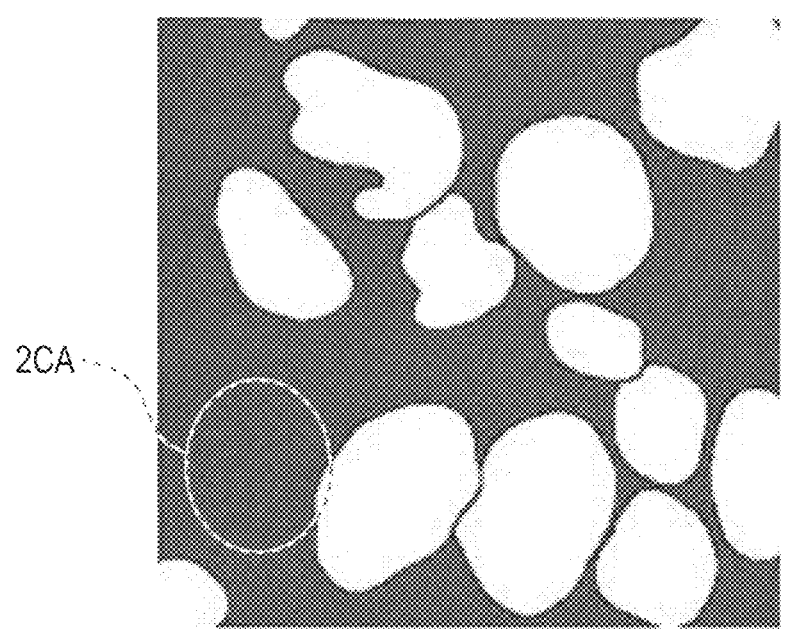
FIG. 6 is a diagram exemplifying a second cell region in the region-identifiable image.

Meanwhile, when the region-identifiable image is acquired by the acquiring unit 211, there may be a difference in the region detected as the first cell region occupied by a specific portion of the cell due to shading of staining in a specific portion of the cell captured in the cell morphological image, a condition of the predetermined image processing in the acquiring unit 211, and the like. For this reason, in some cases, a part of the entire area recognized as the region occupied by the specific portion of the cell in the cell morphological image may not be detected as the first cell region occupied by a specific portion of the cell. For example, as illustrated in FIG. 6, although a region surrounded by the dotted line 2CA is the region to be detected by the acquiring unit 211 as the first cell region, it is not detected as the first cell region. That is, a part of the region that is not detected by the acquiring unit 211 as the first cell region is a region (also referred to as a "second cell region") occupied by a specific portion of the cell different from the first cell region. In this regard, for example, if a display element that identifies the second cell region as a part of the region that is not detected by the acquiring unit 211 as the first cell region in response to a user's manipulation or the like is added to the region-identifiable image, it is possible to more accurately extract overall cell regions from the cell morphological image.

The adding unit 213 adds, to the region-identifiable image, a display element (also referred to as a second display element) that identifies at least an outline portion of the region (second cell region) occupied by the specific portion of the cell different from the first cell region in the cell morphological image depending on a predetermined signal input to the input unit 22. The predetermined signal may be set in advance. For example, a signal for specifying an outline portion of the second cell region may be employed.

For example, a case may be conceived in which a curve is drawn along the outline portion of the second cell region on the cell morphological image through a user's manipulation on the input unit 22 or the like while the cell morphological image is displayed on the display unit 23. In this case, the second display element includes a curved portion that identifies the outline of the second cell region. In this case, the curve may be drawn along the outline portion of the second cell region through a user's manipulation on the input unit 22 or the like, for example, while a state in which the first display element is overlappingly displayed on the cell morphological image and a state in which only the cell morphological image is displayed are switched on the display unit 23. Specifically, a curve may be drawn along a track of a mouse pointer, for example, by moving the mouse pointer along the outline portion of the second cell region while pressing a left mouse button on the cell morphological image of the display unit 23.

The correcting unit 214 corrects the region-identifiable image for an area of the first cell region overlapping with the second cell region (also referred to as an "overlapping area"). Here, the region-identifiable image is corrected by the display control unit 212 for the overlapping area, for example, such that a display element that identifies the first cell region instead of a display element that identifies the second cell region is displayed on the display unit 23. Specifically, the region-identifiable image is corrected such that, for the overlapping area, the display element that identifies the first cell region is displayed with a higher priority than that of the display element that identifies the second cell region, for example, in a default state unless a correction mode is specified in particular.

As a result, a user can easily add the second display element that identifies the second cell region to the region-identifiable image that identifies the first cell region occupied by a specific portion of the cell in the cell morphological image using the first display element. Accordingly, it is possible more easily and accurately extract overall cell regions from the cell morphological image.

The setting unit 215 sets a width of the gap provided between the display element that identifies the first cell region and the display element that identifies the second cell region of the region-identifiable image when the region-identifiable image is corrected for the overlapping area. In the setting unit 215, for example, the width of the gap may be automatically set or may be set depending on a signal input to the input unit 22 in response to a user's operation.

Here, if the width of the gap is narrow, a boundary between the display areas can be recognized, and the feature amount can be obtained with high accuracy through the analysis process. However, when a user tries to see the region-identifiable image, and the width of the gap is wide at a certain degree, it is possible to easily recognize a situation that the display element relating to the first cell region and the display element relating to the second cell region are separated from each other. For example, if the width of the gap is set to 1 μm or larger, it is possible to secure visibility. For this reason, if the width of the gap is set by a user, it is possible to balance accuracy and visibility in the analysis process.

In addition, when the width of the gap is automatically set, the width of the gap may be, for example, a simple fixed width or may be set depending on some parameters such as an occupation ratio between the first and second cell regions in the cell morphological image.

(1-4) Overview of Correction of Region-Identifiable Image

Figure 7:
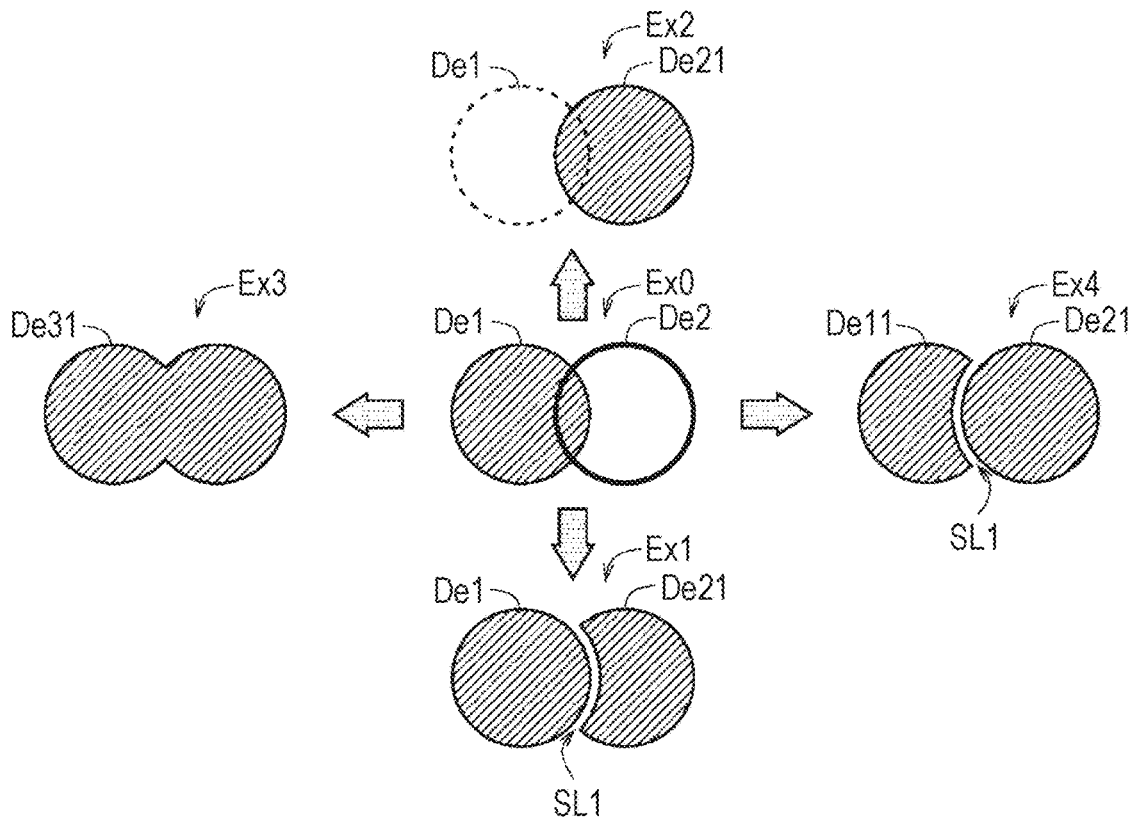
FIG. 7 is a diagram for describing an overview of correction of the region-identifiable image.

FIG. 7 is a diagram for describing an overview of correction of the region-identifiable image using the correcting unit 214. FIG. 7 exemplifies a situation that the region-identifiable image is corrected from a state Ex0 (also referred to as an "addition state") in which a second display element De2 that identifies an outline portion of the second cell region is added to partially overlap with the first display element De1 that identifies the first cell region. In the addition state Ex0 of FIG. 7, the second display element De2 is drawn in a substantially circular shape with a bold line along the outline portion of the second cell region. That is, in FIG. 7, for example, in a case where each of the plurality of first cell regions occupied by a specific portion of the cell in the cell morphological image is identified by the first display element De1 as illustrated in the region-identifiable image of FIG. 5, the bold line as the second display element De2 drawn along the outline portion of the second cell region in the cell morphological image is added to one of the first display elements De1. Specifically, FIG. 7 illustrates, for example, a state Ex0 (addition state) in which the second display element De2 is added to one of the first display elements De1 having a substantially circular shape out of the region-identifiable image of FIG. 5.

The region-identifiable image is corrected depending on at least one of the signal input from a user and the state of the second display element De2, for example, when or after the second display element De2 is added to the region-identifiable image as illustrated in the addition state Ex0 of the center of FIG. 7. For example, a correction mode relating to the overlapping area of the region-identifiable image may be specified depending on a signal input to the input unit 22 in response to a user's operation.

(1-4-1) First Correction (for Preferentially Displaying Display Element Relating to First Cell Region)

For example, unless the correction mode is specified in particular, the region-identifiable image is corrected from the addition state Ex0 to the correction state Ex1 (also referred to as a "first correction state") as illustrated in the lower side of FIG. 7. In this case, for the overlapping area, the region-identifiable image is corrected such that the display element that identifies the first cell region (here, the first display element De1) is preferentially displayed. Here, the correcting unit 214 corrects the region-identifiable image, for example, such that the first display element De1 that identifies the first cell region is displayed by the display control unit 212 on the display unit 23 across the entire overlapping area. In this case, the correcting unit 214 deletes the display element that identifies the second cell region such that the display element that identifies the first cell region is displayed by the display control unit 212 on the display unit 23 across the entire overlapping area.

In this configuration, for example, as illustrated in the first correction state Ex1 of FIG. 7, the display element De21 that identifies the second cell region can be easily added to the region-identifiable image by a user. As a result, it is possible to easily and accurately extract overall cell regions from the cell morphological image. Note that the display element De21 identifies a remaining area obtained by excluding the portions corresponding to the overlapping area from the area surrounded by the second display element De2. For example, the display element De21 is drawn with a predetermined color or hatching. However, if a gap SL1 is provided between the first display element De1 that identifies the first cell region and the display element De21 that identifies the second cell region in the region-identifiable image using the correcting unit 214, it is possible to easily recognize the boundary between the display elements De1 and the De21.

(1-4-2) Second Correction (for Substituting Display Elements Relating to Cell Regions)

For example, if a correction mode for substituting the display element that identifies the first cell region with the display element that identifies the second cell region is specified, the region-identifiable image is corrected from the addition state Ex0 to the correction state Ex2 (also referred to as a "second correction state") illustrated in the upper side of FIG. 7. In this case, the region-identifiable image is corrected by substituting the first display element De1 that identifies the first cell region with the display element De21 that identifies the second cell region including the overlapping area. In this case, the correcting unit 214 corrects the region-identifiable image, for example, such that the display element De21 that identifies the second cell region instead of the first display element De1 that identifies the first cell region in the region-identifiable image is displayed by the display control unit 212 on the display unit 23 depending on a predetermined signal set in advance and input to the input unit 22.

In this configuration, for example, as illustrated in the second correction state Ex2 of FIG. 7, it is possible to easily change the display element that identifies the cell region by a user. As a result, it is possible to easily and accurately extract overall cell regions from the cell morphological image. Note that the display element De21 may be drawn, for example, in the area surrounded by the second display element De2 with a predetermined color or hatching.

(1-4-3) Third Correction (for Expanding Display Elements Relating to Cell Regions)

For example, if the second display element De2 including the curved portion for identifying the outline of the second cell region is not a closed curve in the region-identifiable image, and both ends of the curved portion are placed within an area corresponding to the first cell region, the region-identifiable image is corrected from the addition state Ex0 to the correction state Ex3 (also referred to as a "third correction state") illustrated in the left side of FIG. 7. In this case, the region-identifiable image is corrected such that the first display element De1 that identifies the first cell region is changed to the display element De31 that identifies the area obtained by adding the second cell region to the first cell region (also referred to as an "expanded area"). In this case, for example, the correcting unit 214 changes the first display element that identifies the first cell region into a display element that represents a single area obtained by adding the first and second cell regions if both ends of the curved portion as the second display element De2 are placed within the area corresponding to the first cell region in the region-identifiable image. As a result, the first display element De1 that identifies the first cell region is expanded to the display element De31.

In this configuration, for example, as illustrated in the third correction state Ex3 of FIG. 7, the display element that identifies the cell region can be easily changed by a user. As a result, it is possible to easily and accurately extract overall cell regions from the cell morphological image. Note that the display element De31 may be drawn, for example, in the same shape as that of the first display element De1.

(1-4-4) Fourth Correction (for Preferentially Displaying Display Element Relating to Second Cell Region)

For example, if a correction mode for preferentially displaying the display element that identifies the added second cell region relative to the display element that identifies the first cell region is specified, the region-identifiable image is corrected from the addition state Ex0 to the correction state Ex4 (also referred to as a "fourth correction state") illustrated in the right side of FIG. 7. In this case, for the overlapping area, the region-identifiable image is corrected such that the display element De21 that identifies the second cell region is preferentially displayed. In this case, the correcting unit 214 corrects the region-identifiable image, for example, such that the display element De21 that identifies the second cell region is displayed by the display control unit 212 on the display unit 23 across the entire overlapping area in response to a specific signal set in advance and input to the input unit 22. In this case, the correcting unit 214 deletes the display element that identifies the first cell region, for example, in a portion of the overlapping area where the display element that identifies the second cell region is displayed by the display control unit 212 on the display unit 23. As a result, the first display element De1 can be changed to the display element De11 obtained by excluding the portions corresponding to the overlapping area from the first display element De1. In this case, the correcting unit 214 deletes the display element that identifies the first cell region, for example, such that the display element that identifies the second cell region is displayed by the display control unit 212 on the display unit 23 across the entire overlapping area.

In this configuration, for example, as illustrated in the fourth correction state Ex4 of FIG. 7, a user can easily add the display element De21 that identifies the second cell region to the region-identifiable image. As a result, it is possible to easily and accurately extract overall cell regions from the cell morphological image. Note that the display element De21 may be drawn, for example, in the area surrounded by the second display element De2 with a predetermined color or hatching. In addition, for example, the display element De11 identifies a remaining area obtained by excluding the portions corresponding to the overlapping area from the first display element De1. The display element De11 is drawn, for example, with a predetermined color or hatching. However, if a gap SL1 between the display element De11 that identifies the first cell region and the display element De21 that identifies the second cell region on the region-identifiable image is provided by the correcting unit 214, it is possible to easily recognize the boundary between the display elements De11 and De21.

(1-5) Operation Flow Relating to Correction of Region-Identifiable Image

FIGS. 8 to 12 are flowcharts illustrating an operation flow of the image processing apparatus 2. FIGS. 13 to 33 are diagrams schematically illustrating a specific example of correction of the region-identifiable image using the image processing apparatus 2. The operation flow of the image processing apparatus 2 will now be described with reference to FIGS. 13 to 33 as appropriate.

Figure 8:
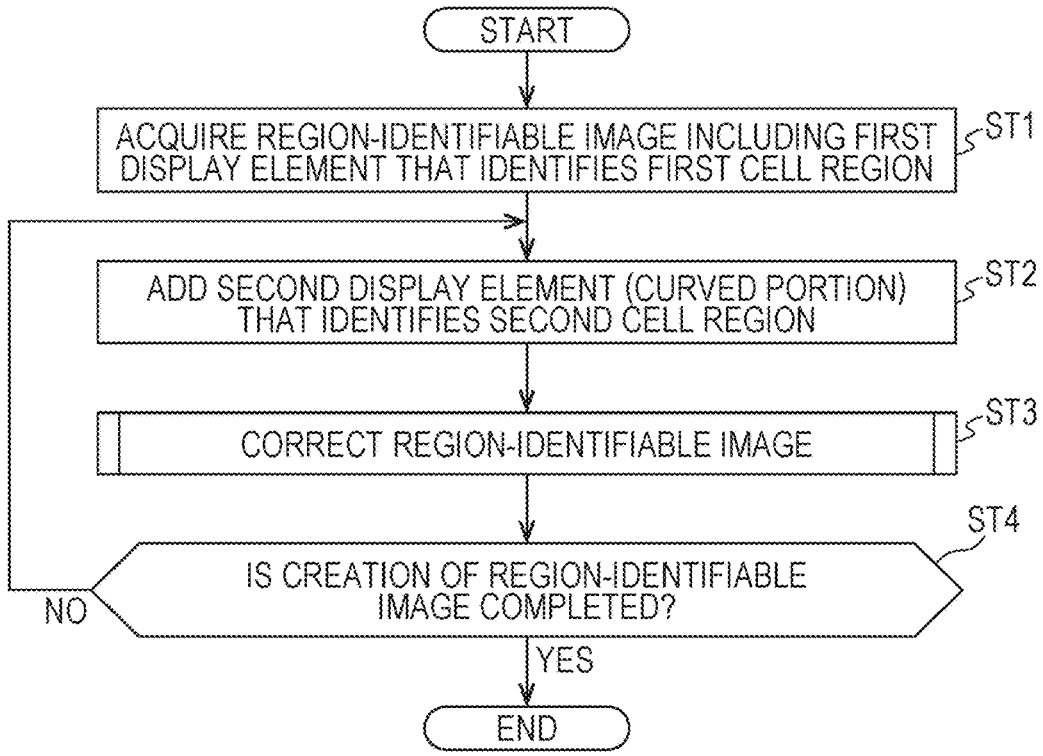
FIG. 8 is a flowchart exemplifying an operation flow of the image processing apparatus.

As illustrated in FIG. 8, the image processing apparatus 2 sequentially performs the processing of steps ST1 to ST4. In other words, the image processing method of the image processing apparatus 2 has steps ST1 to ST4.

In step ST1, the acquiring unit 211 acquires the region-identifiable image in which the first cell region occupied by the specific portion of the cell is identified by the first display element in the cell morphological image. Here, for example, the region-identifiable image illustrated in FIG. 5 is acquired through a predetermined image processing or the like for the cell morphological image illustrated in FIG. 4.

In step ST2, the adding unit 213 adds, to the region-identifiable image, the second display element that identifies at least the outline portion of the second cell region occupied by a specific portion different from the first cell region in the cell morphological image depending on a predetermined signal set in advance and input in response to a user's operation. Here, for example, the curved portion as the second display element that identifies the outline portion of the second cell region occupied by the specific portion that is not captured in the region-identifiable image of FIG. 5 is added to the region-identifiable image while referring to the cell morphological image of FIG. 4. In this case, for example, the second display element that identifies the outline portion of the area surrounded by the dotted line 2CA in FIG. 6 may be added to the region-identifiable image.

In step ST3, the correcting unit 214 corrects the region-identifiable image such that, for the overlapping area of the first cell region overlapping with the second cell region, the display element that identifies the first cell region rather than the display element that identifies the second cell region is displayed on the display unit 23. However, the correction mode of the region-identifiable image may be changed appropriately depending on at least one of the signal input in response to a user's operation and the state of the second display element. Specifically, in step ST3, the region-identifiable image is corrected depending on the operation flow illustrated in FIGS. 9 to 12. Here, a case where the second display element includes a curved portion that identifies the outline of the second cell region will be described by way of example.

Figure 9:
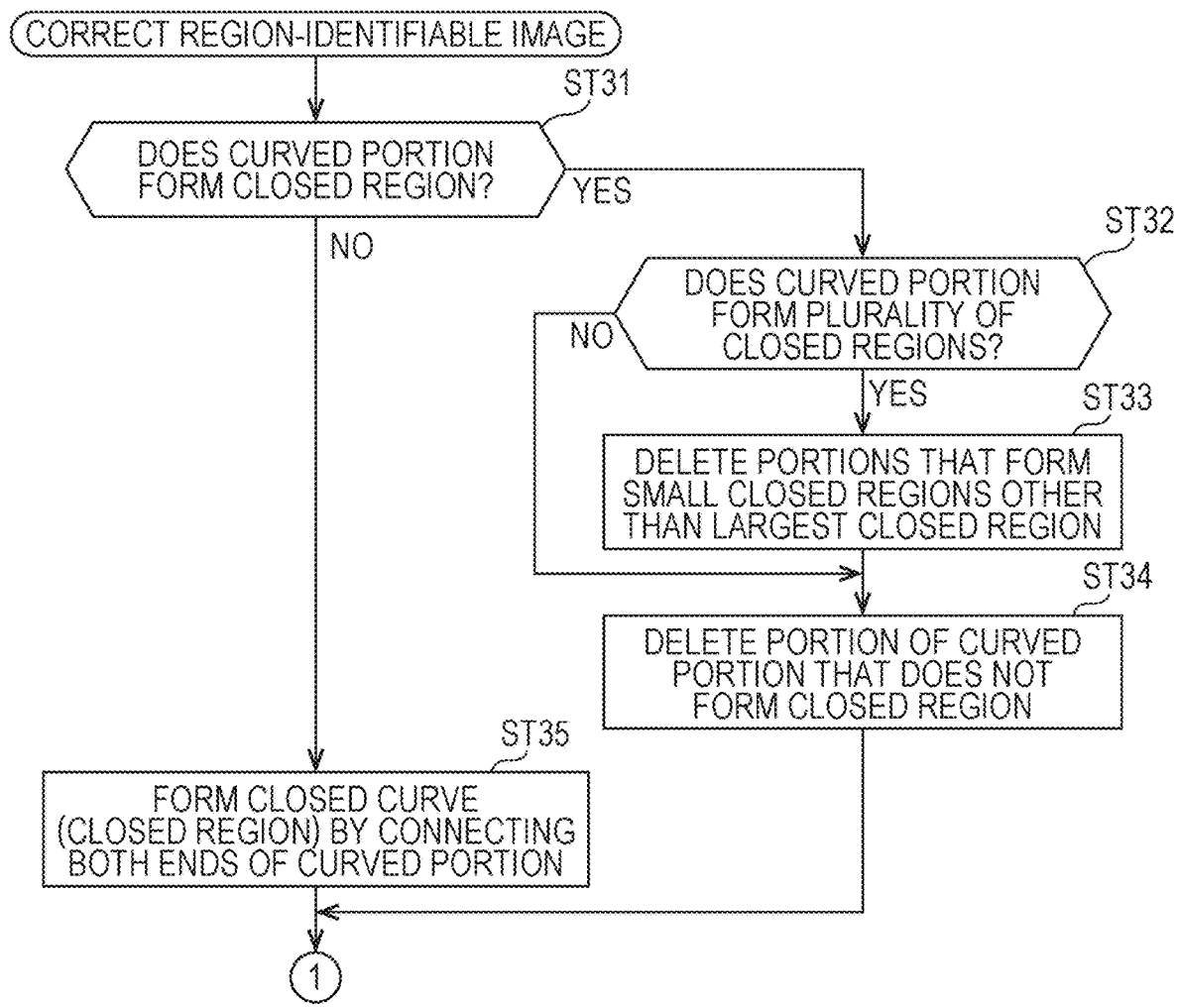
FIG. 9 is a flowchart exemplifying an operation flow of the image processing apparatus.

First, in step ST31 of FIG. 9, it is determined whether or not the curved portion as the second display element De2 forms a closed region. Here, if the curved portion forms the closed region, the process advances to step ST32. If the curved portion does not form the closed region, the process advances to step ST35.

In step ST32, it is determined whether or not the curved portion forms a plurality of closed regions. Here, if the curved portion forms a plurality of closed regions, the process advances to step ST33. If the curved portion does not form a plurality of closed regions, the process advances to step ST34.

Figure 13:
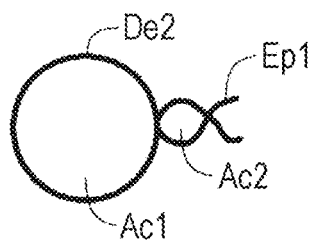
FIG. 13 is a diagram schematically illustrating a specific example of correction of the region-identifiable image.
Figure 14:
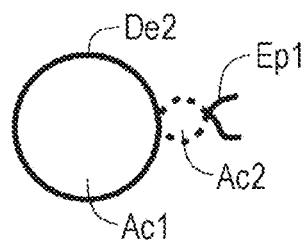
FIG. 14 is a diagram schematically illustrating a specific example of correction of the region-identifiable image.

In step ST33, out of a plurality of closed regions included in the curved portion, portions that form small closed regions other than the largest closed region are deleted. In this case, for example, it is assumed that the curved portion as the second display element De2 forms a pair of closed regions Ac1 and Ac2 as illustrated in FIG. 13. In this case, as illustrated in FIG. 14, out of a plurality of closed regions, a portion that forms a small closed region Ac2 other than the largest closed region Ac1 is deleted from the curved portion.

Figure 15:
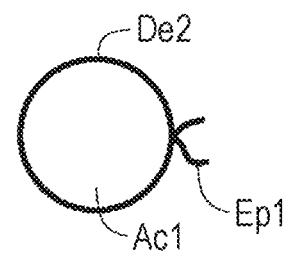
FIG. 15 is a diagram schematically illustrating a specific example of correction of the region-identifiable image.
Figure 16:
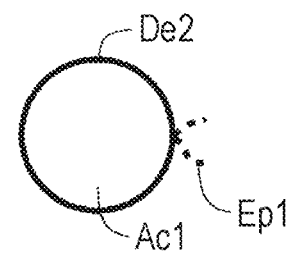
FIG. 16 is a diagram schematically illustrating a specific example of correction of the region-identifiable image.

In step ST34, the portion Ep1 of the curved portion that does not form the closed region is deleted. For example, in a case where the process has progressed from step ST32, a portion Ep1 of the second display element De2 that does not form the closed region Ac1 is deleted as illustrated in FIGS. 15 and 16. Then, the process advances to step ST36 of FIG. 10.

Figure 17:
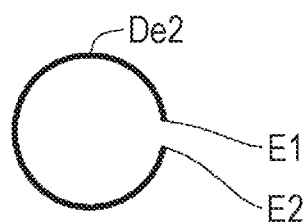
FIG. 17 is a diagram schematically illustrating a specific example of correction of the region-identifiable image.
Figure 18:
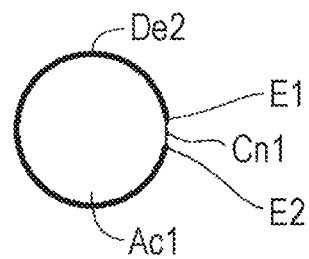
FIG. 18 is a diagram schematically illustrating a specific example of correction of the region-identifiable image.

In step ST35, the closed region Ac1 is formed by connecting both ends of the curved portion. For example, as illustrated in FIGS. 17 and 18, both ends (specifically, one end E1 and another end E2) of the curved portion as the second display element De2 are connected with a line Cn1. Here, the line Cn1 may include, for example, a curved line or a straight line. In FIG. 18, both ends of the curved portion are connected with a straight line Cn1. Then, the process advances to step ST36 of FIG. 10.

Figure 10:
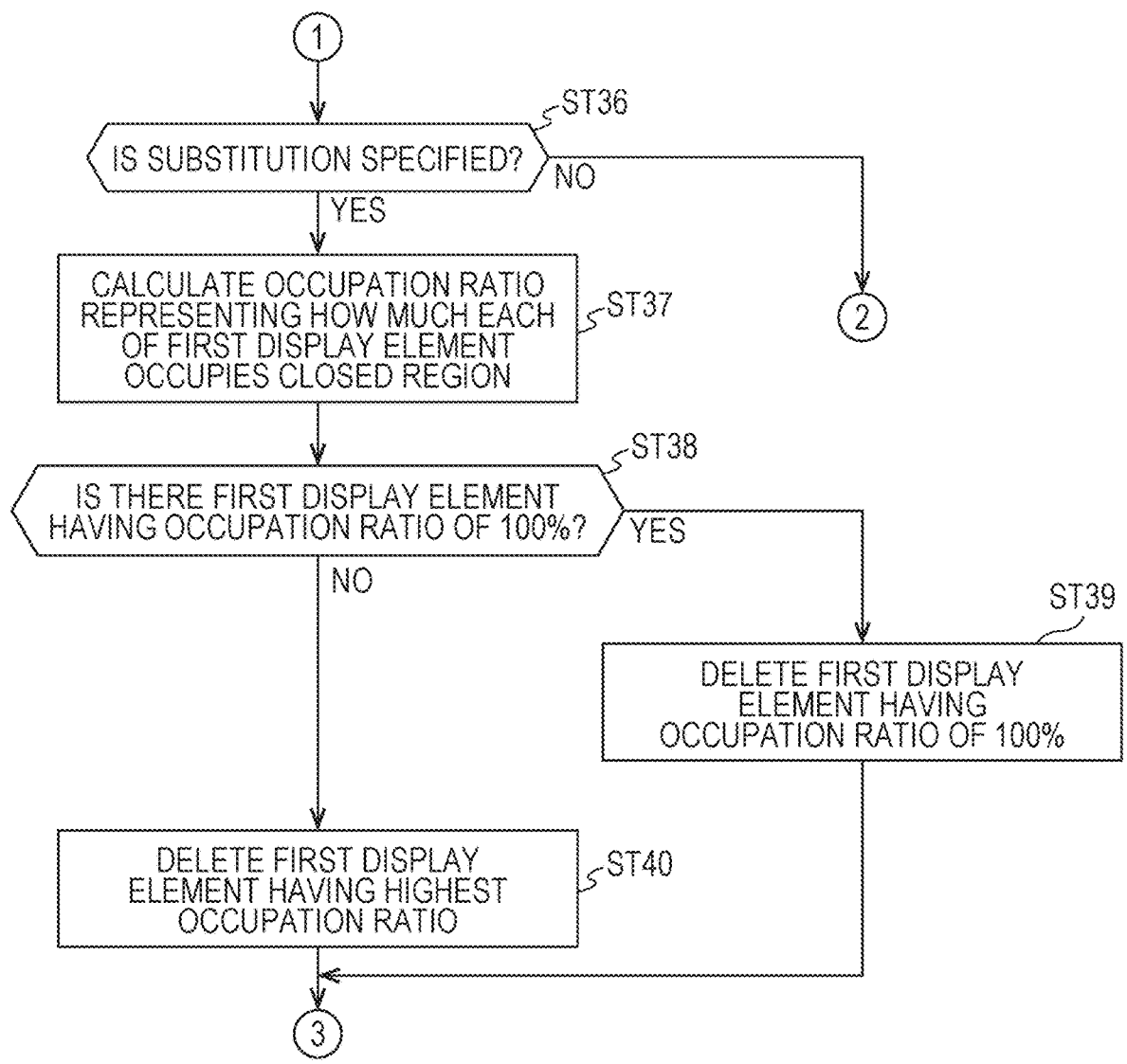
FIG. 10 is a flowchart exemplifying an operation flow of the image processing apparatus.
Figure 11:
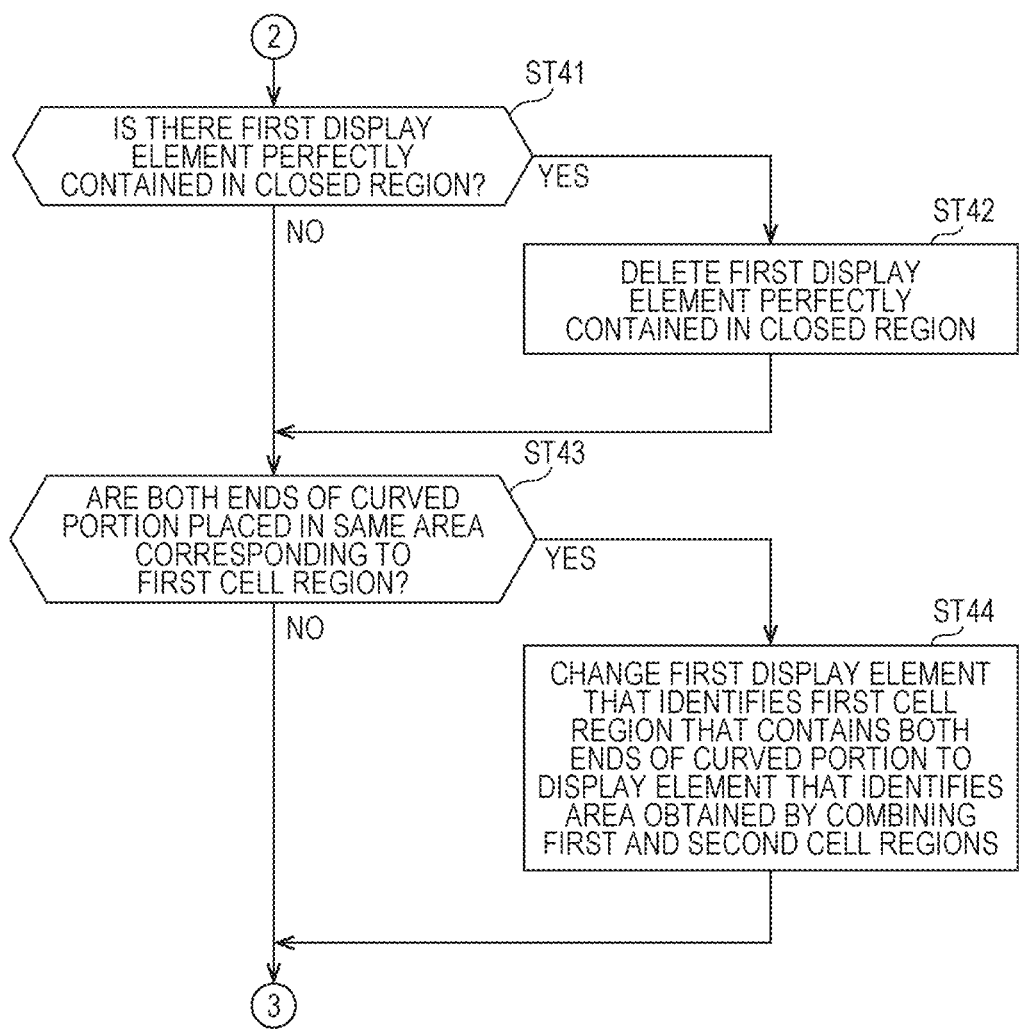
FIG. 11 is a flowchart exemplifying an operation flow of the image processing apparatus.

Then, in step ST36 of FIG. 10, it is determined whether or not a process of substituting the first display element De1 that identifies the first cell region with the second display element De2 that identifies the second cell region (also referred to as a "substitution process") is specified. Here, for example, if the substitution process is specified, the process advances to step ST37. If the substitution process is not specified, the process advances to step ST41 of FIG. 11.

In step ST37, for each of the first display elements De1, an occupation ratio representing how much it occupies the closed region Ac1 formed by the second display element De2 that identifies the second cell region is calculated.

In step ST38, it is determined whether or not there is a first display element De1 having an occupation ratio of 100% calculated in step ST37. Here, if there is the first display element De1 having an occupation ratio of 100%, the process advances to step ST39. If there is no first display element De1 having an occupation ratio of 100%, the process advances to step ST40.

Figure 19:
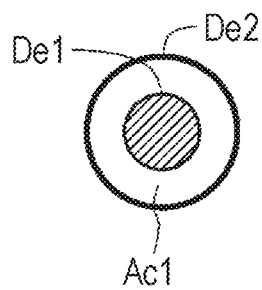
FIG. 19 is a diagram schematically illustrating a specific example of correction of the region-identifiable image.
Figure 20:
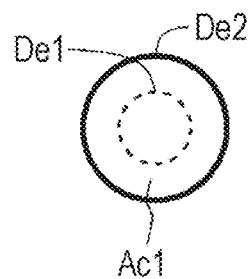
FIG. 20 is a diagram schematically illustrating a specific example of correction of the region-identifiable image.

In step ST39, the first display element De1 having an occupation ratio of 100% is deleted. For example, as illustrated in FIGS. 19 and 20, the first display element De1 perfectly contained in the closed region Ac1 of the second display element De2 is deleted. After the deletion, the process advances to step ST45 of FIG. 12.

Figure 21:
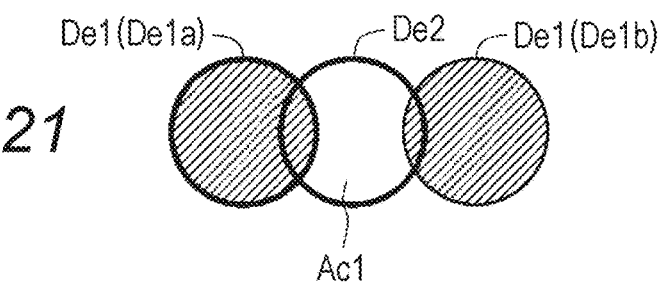
FIG. 21 is a diagram schematically illustrating a specific example of correction of the region-identifiable image.
Figure 22:
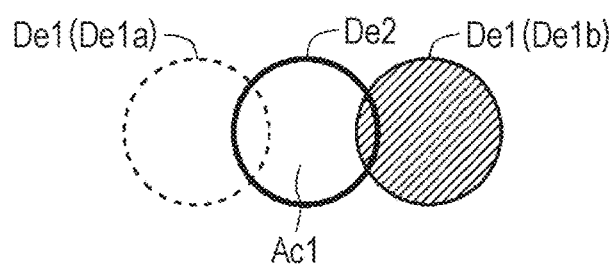
FIG. 22 is a diagram schematically illustrating a specific example of correction of the region-identifiable image.

In step ST40, the first display element De1 having the highest occupation ratio calculated in step ST37 is deleted. For example, in a case where a pair of first display elements De1 (De1a and De1b) are contained in the closed region Ac1 of the second display element De2 as illustrated in FIGS. 21 and 22, the first display element De1 (De1a) having a relatively high occupation ratio is deleted. After the deletion, the process advances to step ST45 of FIG. 12.

Figure 23:
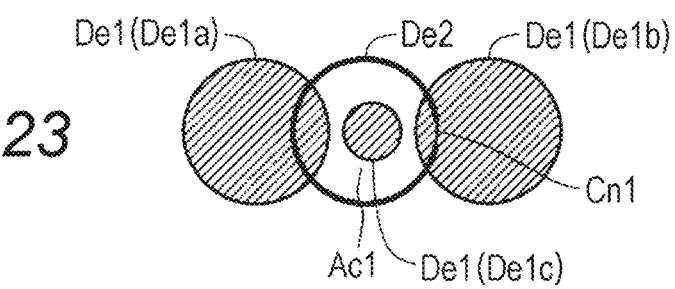
FIG. 23 is a diagram schematically illustrating a specific example of correction of the region-identifiable image.

In step ST41, it is determined whether or not there is a first display element De1 perfectly contained in the closed region Ac1 of the second display element De2. Here, if there is the first display element De1 perfectly contained in the closed region Ac1, the process advances to step ST42. If there is no first display element De1 perfectly contained in the closed region Ac1, the process advances step ST43. For example, if one (De1c) of three first display elements De1 (De1a to De1c) is perfectly contained in the closed region Ac1 as illustrated in FIG. 23, it is possible to determine that there is the first display element De1 perfectly contained in the closed region Ac1.

Figure 24:
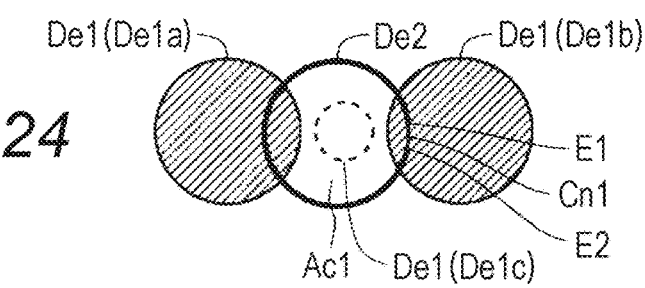
FIG. 24 is a diagram schematically illustrating a specific example of correction of the region-identifiable image.

In step ST42, the first display element De1 perfectly contained in the closed region Ac1 is deleted. For example, as illustrated in FIGS. 23 and 24, the first display element De1 (De1c) perfectly contained in the closed region Ac1 is deleted.

In step ST43, it is determined whether or not both ends of the curved portion of the second display element De2 are placed in the same area corresponding to the first cell region. Here, if both ends of the curved portion are placed in the same area corresponding to the first cell region, the process advances to step ST44. If both ends of the curved portion are not placed in the same area corresponding to the first cell region, the process advances to step ST45 of FIG. 12. For example, FIG. 24 illustrates that both ends of the curved portion of the second display element De2 (specifically, one end E1 and the other end E2) are placed in the first display element De1 (De1b) representing the same area corresponding to the first cell region.

Figure 25:
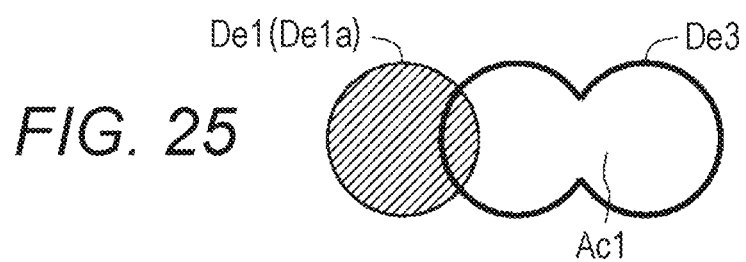
FIG. 25 is a diagram schematically illustrating a specific example of correction of the region-identifiable image.

In step ST44, the first display element that identifies the first cell region that contains both ends of the curved portion as the second display element De2 is changed to a display element that identifies the area obtained by combining the first and second cell regions. For example, as illustrated in FIGS. 24 and 25, the first display element De1 (De1b) that identifies the first cell region that contains both ends (one end E1 and the other end E2) of the curved portion as the second display element De2 is changed to the display element De3 that identifies the area obtained by combining the first and second cell regions.

In step ST45, it is determined whether or not there is the first display element De1 partially contained in the closed region Ac1. Here, if there is the first display element De1 partially contained in the closed region Ac1, the process advances to step ST46. If there is no first display element De1 partially contained in the closed region Ac1, the process advances to step ST49. For example, FIG. 22 illustrates a situation that the first display element De1 (De1b) is partially contained in the closed region Ac1 of the second display element De2. FIG. 25 illustrates a situation that the first display element De1 (De1a) is partially contained in the closed region Ac1 of the display element De3.

In step ST46, it is determined whether or not a correction mode for preferentially displaying the display element De3 and the second display element De2 that identifies the added second cell region relative to the display element that identifies the first cell region is specified depending on a user's operation. Here, if the correction mode for preferentially displaying the display element De3 and the second display element De2 relative to the display element that identifies the first cell region is specified, the process advances to step ST47. If this correction mode is not specified, the process advances to step ST48.

Figure 26:
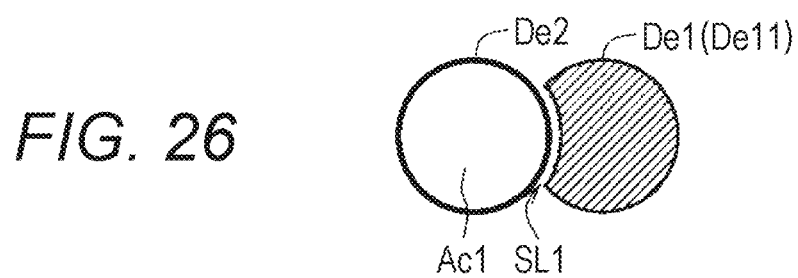
FIG. 26 is a diagram schematically illustrating a specific example of correction of the region-identifiable image.
Figure 27:
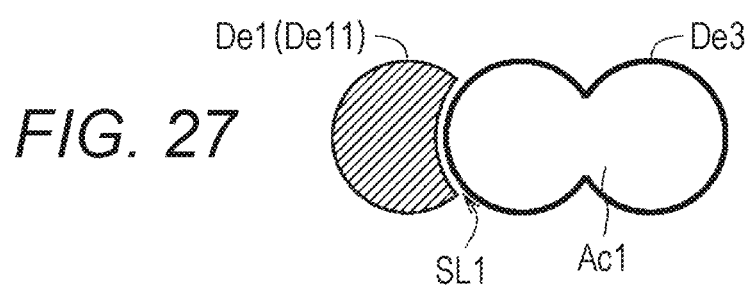
FIG. 27 is a diagram schematically illustrating a specific example of correction of the region-identifiable image.

In step ST47, a portion of the first display element De1 contained in the closed region Ac1 is deleted. For example, as illustrated in FIGS. 22 and 26, a portion of the first display element De1 (De1b) contained in the closed region Ac1 of the second display element De2 is deleted. As a result, the first display element De1 (De1b) is changed to the display element De11 relating to the first cell region. In addition, in this case, for example, a gap SL1 is provided between the display element De11 and the second display element De2. As a result, the region-identifiable image can be an image in which the display elements De11 and the second display element De2 are recognizable while the display element De11 and the second display element De2 do not make contact with each other. In addition, for example, as illustrated in FIGS. 25 and 27, a portion of the first display element De1 (De1a) contained in the closed region Ac1 of the display element De3 is deleted. As a result, the first display element De1 (De1a) is changed to the display element De11 relating to the first cell region. In addition, in this case, for example, a gap SL1 is provided between the display elements De11 and De3. As a result, the region-identifiable image can be an image in which the display elements De11 and De3 are easily recognizable while the display elements De11 and De3 do not contact with each other.

Figure 28:
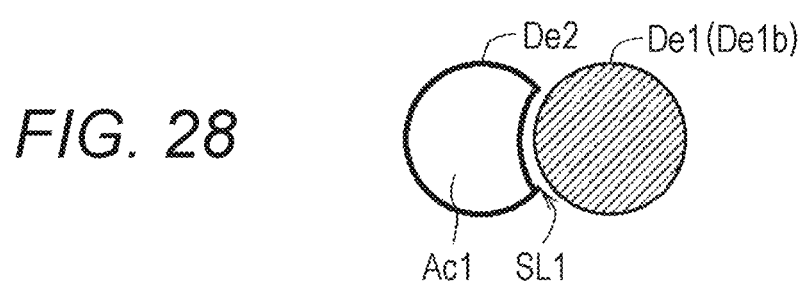
FIG. 28 is a diagram schematically illustrating a specific example of correction of the region-identifiable image.
Figure 29:
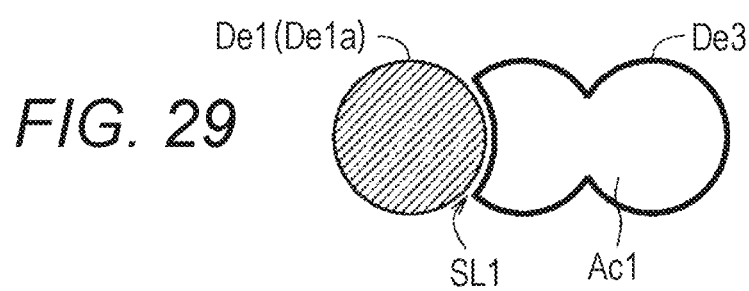
FIG. 29 is a diagram schematically illustrating a specific example of correction of the region-identifiable image.

In step ST48, a portion of the closed curve that forms the closed region Ac1 contained in the first display element De1 is deleted. For example, as illustrated in FIGS. 22 and 28, a portion of the closed curve as the second display element De2 that forms the closed region Ac1 contained in the first display element De1 (De1b) is deleted. In this case, a curve is drawn along the outer edge of the first display element De1 (De1b) such that both ends of the deleted portion of the closed curve as the second display element De2 are connected. Therefore, a state in which the closed region Ac1 is formed by the closed curve is maintained. In addition, in this case, for example, a gap SL1 is provided between the first display element De1 (De1b) and the second display element De2. Furthermore, for example, as illustrated in FIGS. 25 and 29, a portion of the closed curve as the display element De3 that forms the closed region Ac1 contained in the first display element De1 (De1a) is deleted. In this case, a curve is drawn along the outer edge of the first display element De1 (De1a) such that both ends of the deleted portion of the closed curve as the display element De3 are connected. Therefore, a state in which the closed region Ac1 is formed by the closed curve is maintained. In addition, in this case, for example, a gap SL1 is provided between the first display element De1 (De1a) and the display element De3.

Figure 30:
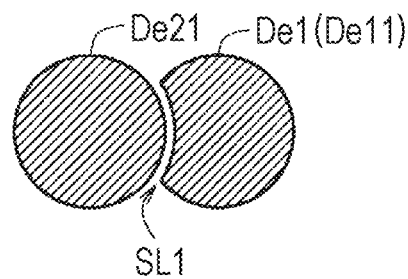
FIG. 30 is a diagram schematically illustrating a specific example of correction of the region-identifiable image.
Figure 31:
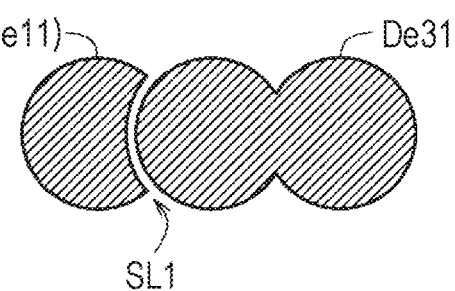
FIG. 31 is a diagram schematically illustrating a specific example of correction of the region-identifiable image.
Figure 32:
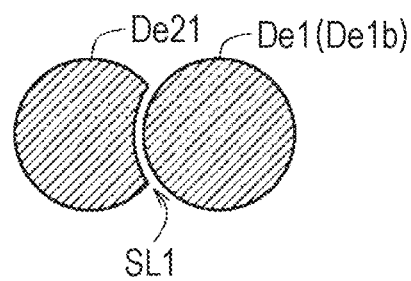
FIG. 32 is a diagram schematically illustrating a specific example of correction of the region-identifiable image.
Figure 33:
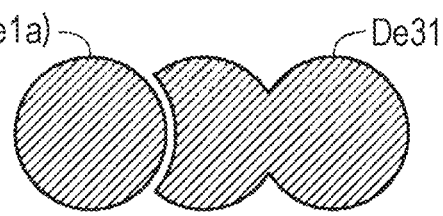
FIG. 33 is a diagram schematically illustrating a specific example of correction of the region-identifiable image.

In step ST49, a display element that identifies the closed region Ac1 is added. Here, for example, a predetermined color or hatching is added to an area surrounded by the closed curve that identifies the closed region Ac1. In this case, the thickness of the closed curve may be adjusted as appropriate. Specifically, for example, the second display element De2 and the closed region Ac1 of FIG. 26 are changed to the display element De21 added with a predetermined color or hatching as illustrated in FIG. 30. As a result, a display element De21 relating to the second cell region is added to the region-identifiable image. In addition, the display element De3 and the closed region Ac1 of FIG. 27 are changed to a display element De31 added with a predetermined color or hatching as illustrated in FIG. 31. As a result, the display element De31 relating to the expanded first cell region is added to the region-identifiable image. In addition, for example, the second display element De2 and the closed region Ac1 of FIG. 28 are changed to the display element De21 added with a predetermined color or hatching as illustrated in FIG. 32. As a result, the display element De21 relating to the second cell region is added to the region-identifiable image. In addition, for example, the display element De3 and the closed region Ac1 of FIG. 29 are changed to the display element De31 added with a predetermined color or hatching as illustrated in FIG. 33. As a result, the display element De31 relating to the expanded first cell region is added to the region-identifiable image.

In step ST4, it is determined whether or not the creation of the region-identifiable image is completed by the control unit 21. Here, for example, it is determined whether or not creation of the region-identifiable image is completed depending on a signal input from the input unit 22 in response to a user's operation. If creation of the region-identifiable image is not completed, the process returns to step ST2. If creation of the region-identifiable image is completed, this operation flow is terminated.

(1-6) Statistics

As described above, in the image processing of the image processing apparatus 2 according to this embodiment, first, the acquiring unit 211 acquires the region-identifiable image that identifies the first cell region occupied by the specific portion of the cell in the cell morphological image using the first display element. Then, the adding unit 213 adds, to the region-identifiable image, the second display element that identifies at least the outline portion of the second cell region occupied by a specific portion other than the first cell region in the cell morphological image depending on a predetermined signal set in advance and input in response to a user's operation. In addition, in the default setting, the correcting unit 214 corrects the region-identifiable image such that the display element that identifies the first cell region rather than the display element that identifies the second cell region is displayed on the display unit 23 for the overlapping area between the first and second cell regions. As a result, it is possible to add a display element that identifies the cell region by a user to the region-identifiable image in which the cell region occupied by the specific portion of the cell in the cell morphological image is identified by the display element. As a result, it is possible to more easily and accurately extract overall cell regions from the cell morphological image.

For example, the processing may be selected as appropriate out of a plurality of processes such as substitution, expansion, and preferential display of the display element performed by the correcting unit 214 depending on a user's operation.

(2) Modifications

Note that the invention is not limited to the aforementioned embodiments, various changes or modifications may be possible without departing from the scope and spirit of the invention.

(2-1) First Modification

For example, according to the aforementioned embodiment, the correcting unit 214 deletes the display element that identifies the second cell region from the area where the display element that identifies the first cell region is displayed in the overlapping area between the first and second cell regions. In addition, the correcting unit 214 deletes the display element that identifies the first cell region from the area where the display element that identifies the second cell region. However, the invention is not limited thereto. For example, the correcting unit 214 may correct the region-identifiable image such that the display element that identifies the first cell region constitutes a base layer, and the display element that identifies the second cell region constitutes a back layer in the area where the display element that identifies the first cell region is displayed in the overlapping area. In addition, the region-identifiable image may be corrected, for example, such that the display element that identifies the second cell region constitutes a front layer in the area where the display element that identifies the second cell region is displayed in the overlapping area. Here, the back layer refers to a layer displayed behind the base layer, and the front layer refers to a layer displayed in front of the base layer. In this configuration, it is possible to clearly recognize a front-rear relationship of the cell regions in the region-identifiable image. In addition, it is possible to easily obtain information of other cell regions hiding behind a certain cell region as necessary.

In a case where a plurality of layers are included in the region-identifiable image, the region-identifiable image may be corrected such that the display element that identifies the first cell region corresponding to the base layer and the display element that identifies the second cell region corresponding to at least one of the front and back layers are displayed in different display modes on the display unit 23. Here, as the different display modes, for example, at least one of brightness, shading, and color may be displayed differently. In this configuration, it is possible to easily distinguish a plurality of display elements that identify neighboring cell regions. Furthermore, even in this configuration, it is possible to recognizably display a boundary between the display elements by providing a gap SL1 between the display element that identifies the first cell region and the display element that identifies the second cell region in the region-identifiable image.

Here, a configuration of providing a plurality of layers in the region-identifiable image will be described by way of specific example.

Figure 12:
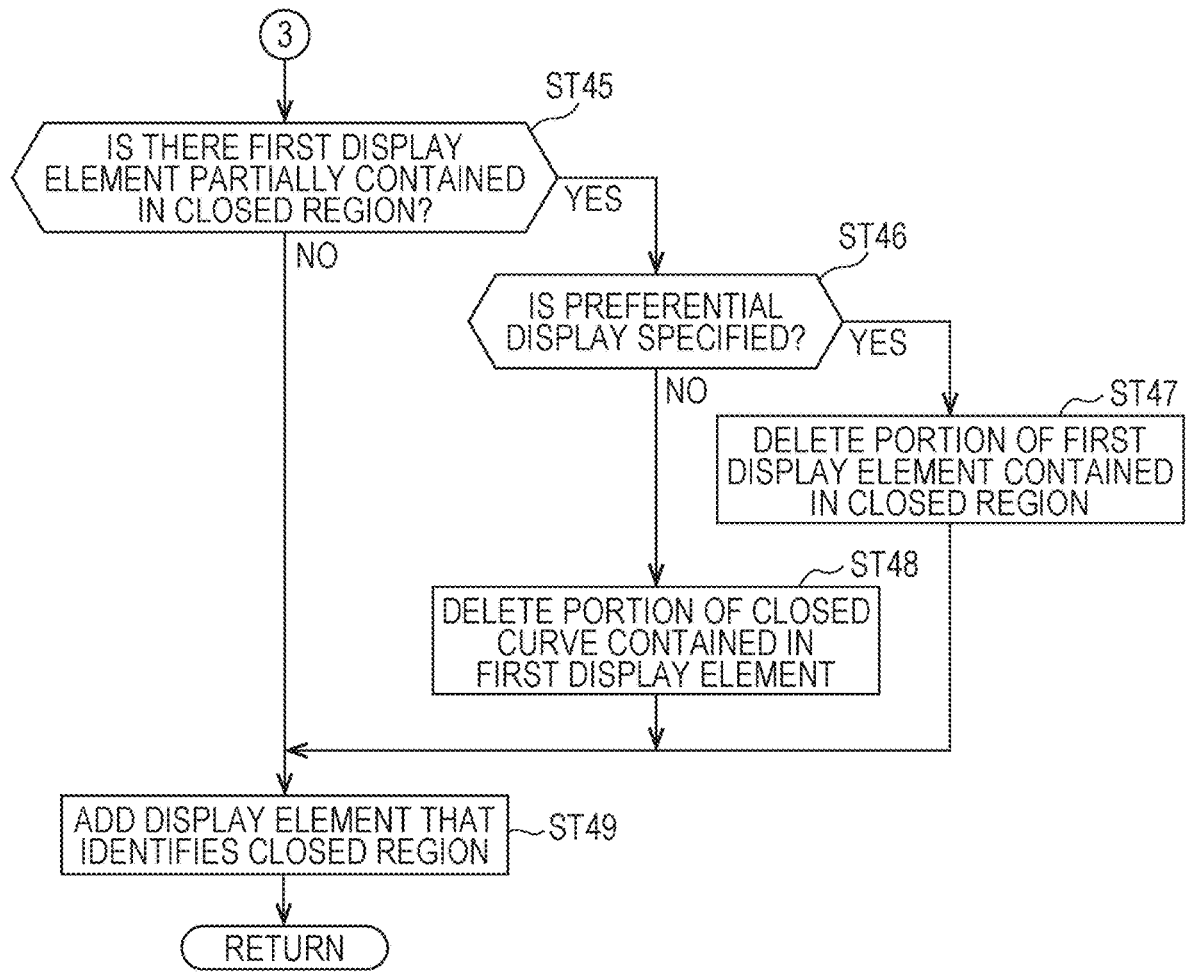
FIG. 12 is a flowchart exemplifying an operation flow of the image processing apparatus.
Figure 34:
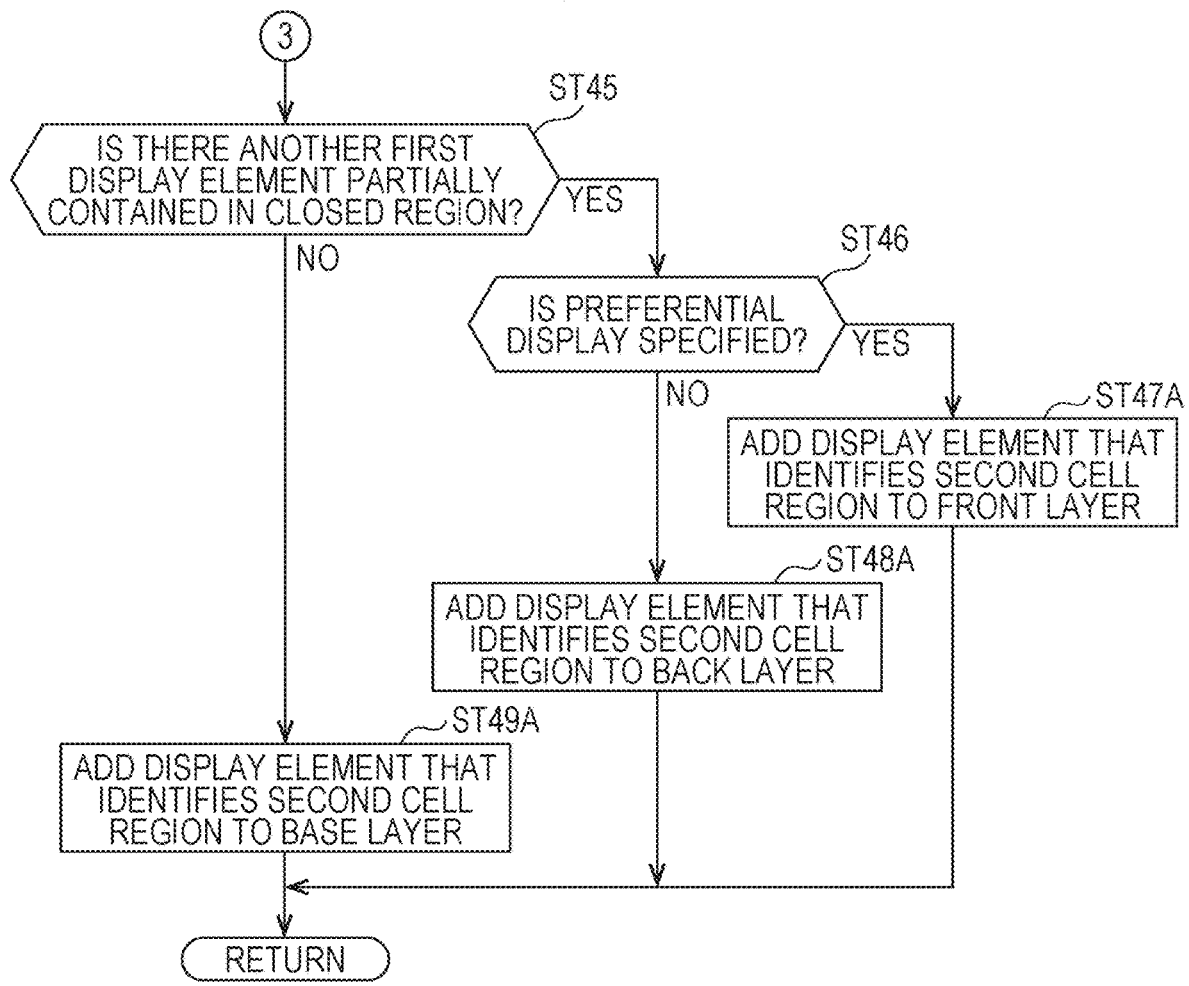
FIG. 34 is a flowchart illustrating an operation flow relating to correction of the region-identifiable image according to a first modification.

FIG. 34 is a flowchart illustrating an operation flow relating to correction of the region-identifiable image according to the first modification. In the operation flow of the image processing apparatus 2 according to this modification, the operation flow of FIG. 12 is substituted with the operation flow of FIG. 34 on the basis of the operation flow of the aforementioned embodiment. Note that, in the operation flow of FIG. 34, steps ST47 to ST49 of the operation flow of FIG. 12 are changed to steps ST47A to ST49A. For this reason, here, the description will be given for steps ST47A to ST49A.

Figure 35:
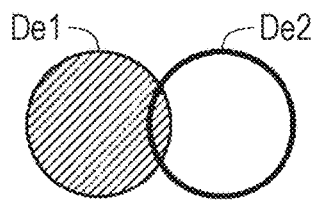
FIG. 35 is a diagram schematically illustrating a specific example of correction of the region-identifiable image according to the first modification.
Figure 36:
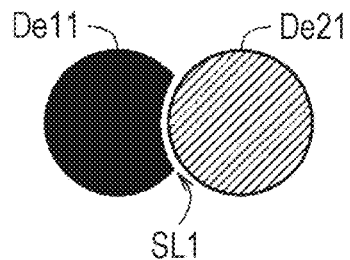
FIG. 36 is a diagram schematically illustrating a specific example of correction of the region-identifiable image according to the first modification.

In step ST47A of FIG. 34, the display element that identifies the second cell region is added to the front layer. Here, for example, if the front layer is not provided, the front layer may be created, and the display element that identifies the second cell region may be added to the front layer. If the front layer already exists, the display element that identifies the second cell region may be added to the front layer. For example, as illustrated in FIGS. 35 and 36, the display element De21 that identifies the second cell region specified by the second display element De2 is added to the front layer in front of the base layer where the first display element De1 is drawn. In this case, for example, the gap SL1 is displayed between the first display element De1 and the display element De21, and the display element De1 drawn on the base layer and the display element De21 drawn of the front layer are displayed in different modes. For example, as illustrated in FIG. 36, an aspect is contemplated in which the display element drawn on the relatively backward layer may be displayed relatively thicker or darker.

Figure 37:
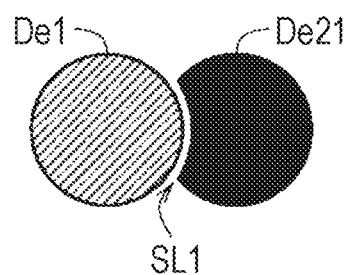
FIG. 37 is a diagram schematically illustrating a specific example of correction of the region-identifiable image according to the first modification.

In step ST48A, the display element that identifies the second cell region is added to the back layer. Here, for example, if the back layer is not provided, the back layer may be created, and the display element that identifies the second cell region may be added to the back layer. If the back layer already exists, the display element that identifies the second cell region may be added to the back layer. For example, as illustrated in FIGS. 35 and 37, the display element De21 that identifies the second cell region specified by the second display element De2 is added to the back layer behind the base layer where the first display element De1 is drawn. In this case, for example, the gap SL1 is displayed between the first display element De1 and the display element De21, and the display element De1 drawn on the base layer and the display element De21 drawn on the back layer are displayed in different modes. For example, as illustrated in FIG. 37, an aspect is contemplated in which the display element drawn on the relatively backward layer may be displayed relatively thicker or darker.

(2-2) Other Modifications

In the aforementioned embodiment, the adding unit 213 adds the curved portion that identifies the outline of the second cell region to the region-identifiable image as the second display element De2. However, the invention is not limited thereto. For example, instead of center-blurred curved portion, a solid region corresponding to the entire second cell region may be added to the region-identifiable image as the second display element that identifies the second cell region. In this case, the outline portion of the second display element of the solid corresponds to the curved portion that identifies the outline of the second cell region.

In the aforementioned embodiment, the display unit 23 is included in the image processing apparatus 2. However, the invention is not limited thereto. For example, the display unit 23 may be an external display device data-communicably connected to the image processing apparatus 2.

In the aforementioned embodiment, if there is no particular specification for the correction mode from a user, the correcting unit 214 corrects the region-identifiable image such that the display element that identifies the first cell region rather than the display element that identifies the second cell region is displayed for the overlapping area. However, the invention is not limited thereto. For example, the correcting unit 214 may correct the region-identifiable image such that the display element that identifies the second cell region is displayed for a part of the overlapping area. That is, for example, the correcting unit 214 may correct the region-identifiable image such that the display element that identifies the first cell region is displayed by the display control unit 212 on the display unit 23 for at least a part of the overlapping area. In this case, the correcting unit 214 deletes the display element that identifies the first cell region, for example, for the area where the display element that identifies the second cell region is displayed by the display control unit 212 on the display unit 23 in the overlapping area. Using this configuration, a user can easily add the display element De21 that identifies the second cell region to the region-identifiable image. As a result, it is possible to easily and accurately extract overall cell regions from the cell morphological image.

In the aforementioned embodiment, if a correction mode for preferentially displaying the display element that identifies the second cell region rather than the display element that identifies the first cell region is specified for the overlapping area, the correcting unit 214 corrects the region-identifiable image such that the display element that identifies the second cell region is displayed across the entire overlapping area. However, the invention is not limited thereto. For example, the correcting unit 214 may correct the region-identifiable image such that the display element that identifies the first cell region is displayed in a part of the overlapping area. That is, for example, the correcting unit 214 may correct the region-identifiable image such that the display element that identifies the second cell region is displayed by the display control unit 212 on the display unit 23 for at least a part of the overlapping area. In this case, for example, the correcting unit 214 deletes the display element that identifies the first cell region for a portion of the overlapping area where the display element that identifies the second cell region is displayed by the display control unit 212 on the display unit 23. Using this configuration, a user can easily add the display element De21 that identifies the second cell region to the region-identifiable image. As a result, it is possible to easily and accurately extract overall cell regions from the cell morphological image.

In the aforementioned embodiment, the cell morphological image is an image capturing a shape of the cell nucleus as the specific portion. However, the invention is not limited thereto. For example, the specific portion may include other portions constituting cells such as cell membranes.

In the aforementioned embodiment, the living body includes animals in a broad sense. However, the invention is not limited thereto. For example, the living body may include plants or the like in addition to animals. That is, the living body may include living organisms encompassing animals and plants.

In the aforementioned embodiment, the acquiring unit 211 acquires the region-identifiable image through a predetermined image processing for the cell morphological image. However, the invention is not limited thereto. For example, the acquiring unit 211 may acquire a region-identifiable image created by an external device other than the image processing apparatus 2 via the communication I/F 24 or the like.

Note that all or a part of elements of the aforementioned embodiments and various modifications may be combined as appropriate unless it is inconsistent.

REFERENCE SIGNS LIST 1 microscopic image acquiring apparatus
2 image processing apparatus
3 communication line
21 control unit
22 input unit
23 display unit
24 communication I/F
25 memory unit
26 bus
100 pathological diagnosis support system
211 acquiring unit
212 display control unit
213 adding unit
214 correcting unit
215 setting unit
Ac1, Ac2 closed region
De1 first display element
De2 second display element
De3, De11, De21, De31 display element
E1 one end
E2 the other end
P1 program
SL1 gap

The invention claimed is:

1. An image processing apparatus comprising:
a display controller that displays a cell morphological image capturing a shape of a cell on a display;
an acquisitor that acquires a region-identifiable image for identifying a first cell region occupied by a specific portion of the cell in the cell morphological image using a first display element;
an inputter that receives a signal responding to a user's operation;
adder that adds, to the region-identifiable image, a second display element that identifies at least an outline portion of a second cell region occupied by the specific portion other than the first cell region in the cell morphological image depending on a predetermined signal set in advance and input to the inputter; and
a corrector configured to correct the region-identifiable image such that a display element that identifies the first cell region is displayed by the display controller on the display unit for at least a part of an overlapping area where the first and second cell regions overlap each other;
wherein the corrector is further configured to provide a gap between the display element that identifies the first cell region and the display element that identifies the second cell region in the region-identifiable image according to an occupation ratio, the occupation ratio representing how much the first display element occupies a closed region formed by the second display element in the cell morphological image.

2. The image processing apparatus according to claim 1, wherein the corrector corrects the region-identifiable image such that the display element that identifies the first cell region is displayed by the display controller on the display across the entire overlapping area.

3. The image processing apparatus according to claim 2, wherein the corrector corrects the region-identifiable image such that the display element that identifies the second cell region is displayed by the display controller on the display for at least a part of the overlapping area in response to a particular signal set in advance and input to the inputter.

4. The image processing apparatus according to claim 2, wherein the corrector deletes the display element that identifies the second cell region from the region-identifiable image for a portion of the overlapping area where the display element that identifies the first cell region is displayed by the display controller on the display, and
the corrector deletes the display element that identifies the first cell region from the region-identifiable image for a portion of the overlapping area where the display element that identifies the second cell region is displayed by the display controller on the display.

5. The image processing apparatus according to claim 2, wherein the corrector provides a gap between the display element that identifies the first cell region and the display element that identifies the second cell region in the region-identifiable image.

6. The image processing apparatus according to claim 2, wherein the corrector corrects the region-identifiable image such that
the display element that identifies the first cell region constitutes a base layer,
the display element that identifies the second cell region constitutes a back layer placed behind the base layer for a portion of the overlapping area where the display element that identifies the first cell region is displayed by the display controller on the display, and
the display element that identifies the second cell region constitutes a front layer placed in front of the base layer for a portion of the overlapping area where the display element that identifies the second cell region is displayed by the display controller on the display.

7. The image processing apparatus according to claim 2, wherein the corrector corrects the region-identifiable image such that the display element that identifies the second cell region instead of the display element that identifies the first cell region in the region-identifiable image is displayed by the display controller on the display in response to a predefined signal set in advance and input to the inputter.

8. The image processing apparatus according to claim 2, wherein the second display element includes a curved portion that identifies an outline of the second cell region, and
the corrector changes the first display element into a display element representing a single area obtained by combining the first and second cell regions depending on whether or not both ends of the curved portion are placed in an area of the region-identifiable image corresponding to the first cell region.

9. A non-transitory recording medium storing a computer readable image processing program executed by a hardware processor included in an information processing apparatus to cause the information processing apparatus to work as the image processing apparatus according to claim 2.

10. The image processing apparatus according to claim 1, wherein the corrector corrects the region-identifiable image such that the display element that identifies the second cell region is displayed by the display controller on the display for at least a part of the overlapping area in response to a particular signal set in advance and input to the inputter.

11. The image processing apparatus according to claim 10, wherein the corrector corrects the region-identifiable image such that the display element that identifies the second cell region is displayed by the display controller on the display across the entire overlapping area in response to the particular signal set in advance and input to the inputter.

12. The image processing apparatus according to claim 1, wherein the corrector deletes the display element that identifies the second cell region from the region-identifiable image for a portion of the overlapping area where the display element that identifies the first cell region is displayed by the display controller on the display, and the corrector deletes the display element that identifies the first cell region from the region-identifiable image for a portion of the overlapping area where the display element that identifies the second cell region is displayed by the display controller on the display.

13. The image processing apparatus according to claim 1, further comprising a setter that sets a width of the gap in response to a signal input to the inputter.

14. The image processing apparatus according to claim 1, wherein the corrector corrects the region-identifiable image such that the display element that identifies the first cell region constitutes a base layer, the display element that identifies the second cell region constitutes a back layer placed behind the base layer for a portion of the overlapping area where the display element that identifies the first cell region is displayed by the display controller on the display, and the display element that identifies the second cell region constitutes a front layer placed in front of the base layer for a portion of the overlapping area where the display element that identifies the second cell region is displayed by the display controller on the display.

15. The image processing apparatus according to claim 14, wherein the corrector corrects the region-identifiable image such that a display mode of the display is different between the display element that identifies the first cell region corresponding to the base layer and the display element that identifies the second cell region corresponding to at least one of the back layer and the front layer.

16. The image processing apparatus according to claim 1, wherein the corrector corrects the region-identifiable image such that the display element that identifies the second cell region instead of the display element that identifies the first cell region in the region-identifiable image is displayed by the display controller on the display in response to a predefined signal set in advance and input to the inputter.

17. The image processing apparatus according to claim 1, wherein the second display element includes a curved portion that identifies an outline of the second cell region, and the corrector changes the first display element into a display element representing a single area obtained by combining the first and second cell regions depending on whether or not both ends of the curved portion are placed in an area of the region-identifiable image corresponding to the first cell region.

18. A non-transitory recording medium storing a computer readable image processing program executed by a hardware processor included in an information processing apparatus causing the information processing apparatus to work as the image processing apparatus according to claim 1.

19. An image processing method comprising:
(a) acquiring a region-identifiable image for identifying a first cell region occupied by a specific portion of a cell in a cell morphological image capturing a shape of the cell using a first display element by an acquisitor;
(b) adding, to the region-identifiable image, a second display element that identifies at least an outline portion of a second cell region occupied by the specific portion other than the first cell region in the cell morphological image depending on a predetermined signal set in advance and input in response to a user's operation by an adder; and
(c) correcting the region-identifiable image such that the display element that identifies the first cell region is displayed on a display for at least a part of the overlapping area where the first and second cell regions overlap each other by a corrector;
wherein the corrector is further configured to provide a gap between the display element that identifies the first cell region and the display element that identifies the second cell region in the region-identifiable image according to an occupation ratio, the occupation ratio representing how much the first display element occupies a closed region formed by the second display element in the cell morphological image.

* * * * *